United States Patent
Fareed Bhutto et al.

(10) Patent No.: US 12,412,323 B2
(45) Date of Patent: Sep. 9, 2025

(54) SYSTEM AND METHOD FOR COMPLEX INPUT DATA CONFIGURATIONS FOR IMAGING APPLICATIONS

(71) Applicants: The General Hospital Corporation, Boston, MA (US); Trustees of Boston University, Boston, MA (US)

(72) Inventors: Danyal Fareed Bhutto, Boston, MA (US); Matthew S. Rosen, Somerville, MA (US); Neha Koonjoo, Boston, MA (US); Bo Zhu, Palo Alto, CA (US)

(73) Assignees: The General Hospital Corporation, Boston, MA (US); Trustees of Boston University, Boston, MA (US)

( * ) Notice: Subject to any disclaimer, the term of this patent is extended or adjusted under 35 U.S.C. 154(b) by 338 days.

(21) Appl. No.: 18/305,697

(22) Filed: Apr. 24, 2023

(65) Prior Publication Data

US 2023/0342996 A1 Oct. 26, 2023

Related U.S. Application Data

(60) Provisional application No. 63/334,077, filed on Apr. 22, 2022.

(51) Int. Cl.
*G06T 11/00* (2006.01)
*A61B 5/055* (2006.01)
*G16H 30/40* (2018.01)

(52) U.S. Cl.
CPC .......... *G06T 11/006* (2013.01); *A61B 5/055* (2013.01); *G16H 30/40* (2018.01); *G06T 2210/41* (2013.01); *G06T 2211/421* (2013.01)

(58) Field of Classification Search
CPC ............ G06T 11/006; G06T 2210/41; G06T 2211/421; G16H 30/40; A61B 5/055
USPC ........................................................ 382/131
See application file for complete search history.

(56) References Cited

U.S. PATENT DOCUMENTS 11,620,772 B2   4/2023   Rosen et al.
2022/0076460 A1*   3/2022   Vaughan, Jr. .......... G16H 50/20

OTHER PUBLICATIONS

Zhu, Bo, et al. "Image reconstruction by domain-transform manifold learning." Nature 555.7697 (2018): 487-492. (Year: 2018).*

* cited by examiner

*Primary Examiner* — Jonathan S Lee
(74) *Attorney, Agent, or Firm* — QUARLES & BRADY LLP

(57) ABSTRACT

Systems, methods, and media for complex input data configurations for imaging applications. Complex data optimization can be provided to improve accuracy of models (e.g., neural networks) used to reconstruct medical images from raw sensor data, for example. Complex data optimization can include applying raw sensor data to an input layer of a neural network to generate an input vector ordered such that real components and imaginary components of samples in the raw sensor data are adjacent. The input vector can then be applied to convolutional layer of the neural network.

20 Claims, 18 Drawing Sheets

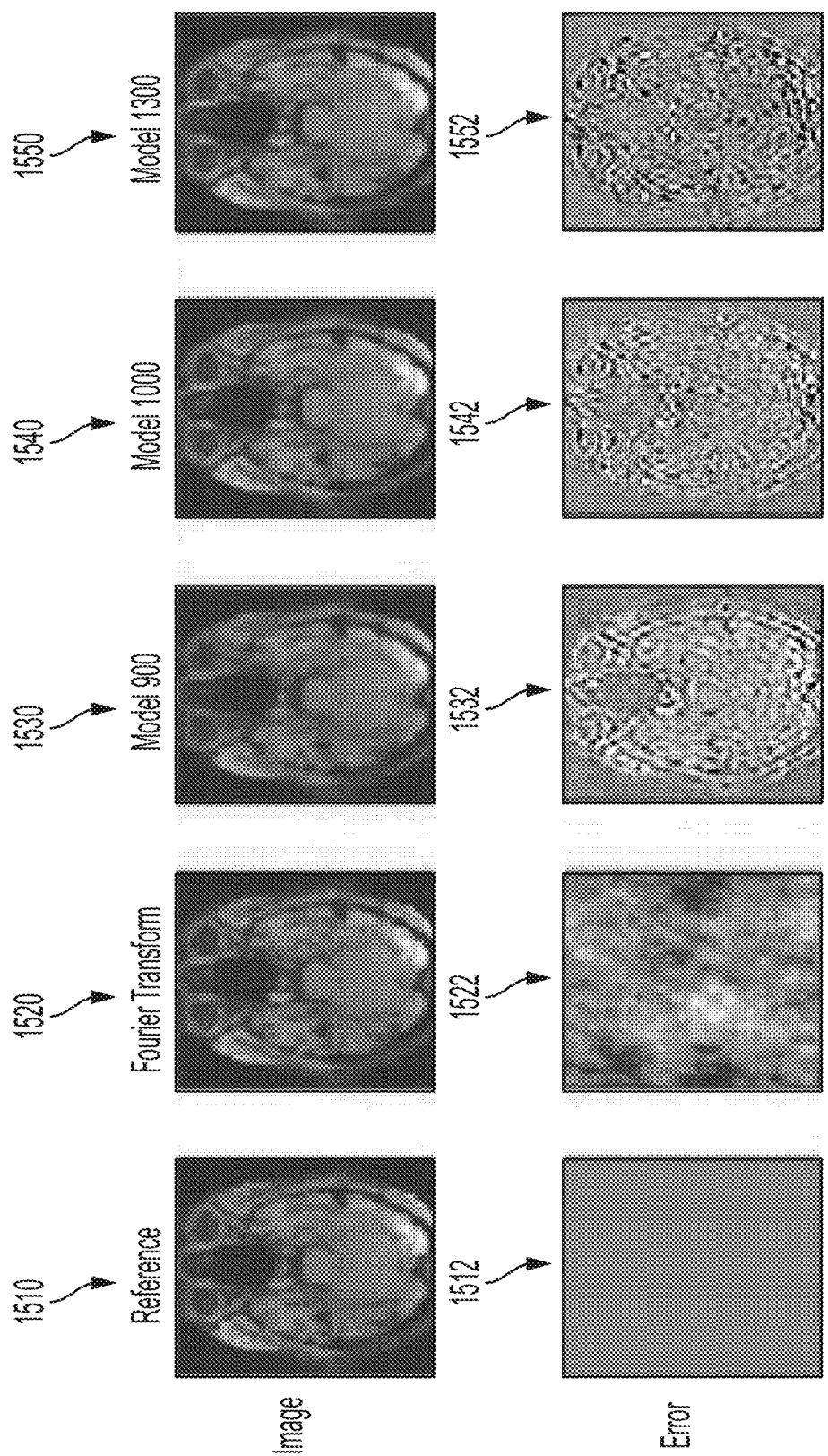

| Approach | Mean Squared Error (MSE) | Root Mean Squared Error (RMSE) |
|---|---|---|
| Fourier Transform | ------- | 21.51% |
| Model 900 | 9.63E-05 | 0.98% |
| Model 1000 | 4.04E-05 | 0.64% |
| Model 1300 | 4.01E-05 | 0.63% |

SYSTEM AND METHOD FOR COMPLEX INPUT DATA CONFIGURATIONS FOR IMAGING APPLICATIONS

CROSS-REFERENCE TO RELATED APPLICATIONS

This application claims the benefit of and priority to U.S. Provisional Patent Application No. 63/334,077, filed Apr. 22, 2022, the entirety of which is incorporated by reference herein.

STATEMENT REGARDING FEDERALLY SPONSORED RESEARCH

This invention was made with government support under Grant No. DGE-1840990 awarded by the National Science Foundation Graduate Research Fellowship and under Grant No. DGE-1633516NSF awarded by the National Science Foundation Research Traineeship Program: Understanding the Brain. The government has certain rights in the invention.

BACKGROUND

The present disclosure relates generally to imaging and, more particularly, to systems, methods, and media for reconstructing medical images from acquired data. The field of medical imaging presents various constraints that are not present in more general fields such as general photography. For example, medical imaging may require appropriate transformation from the sensor or signal domain to the image domain. Improvements in medical imaging technology are generally desired across a wide range of different applications.

SUMMARY

One aspect of the present disclosure is a method for medical imaging. The method includes receiving raw sensor data acquired from a patient using a medical imaging modality; applying the raw sensor data to an input layer of a neural network to generate an input vector, wherein the input layer of the neural network orders the input vector such that a real component and an imaginary component of each sample in the raw sensor data are adjacent to each other; applying the input vector to a first convolutional layer of the neural network to generate a filtered input vector; applying the filtered input vector to at least one fully connected layer of the neural network to generate a matrix; applying the matrix to at least one additional convolutional layer of the neural network different from the first convolutional layer to generate a medical image of the patient; and displaying the medical image of the patient.

Another aspect of the present disclosure is a non-transitory computer-readable storage medium having instructions stored thereon that, when executed by at least one processor, cause the at least one processor to implement operations. The operations include receiving raw sensor data acquired from a patient using a medical imaging system; applying the raw sensor data to an input layer of a neural network to generate an input vector, wherein the input layer of the neural network orders the input vector such that a real component and an imaginary component of each sample in the raw sensor data are adjacent; applying the input vector to a first convolutional layer of the neural network to generate a filtered input vector; applying the filtered input vector to at least one fully connected layer of the neural network to generate a matrix; applying the matrix to at least one additional convolutional layer of the neural network different from the first convolutional layer to generate a medical image of the patient; and displaying the medical image of the patient for clinical analysis.

Yet another aspect of the present disclosure is a system. The system includes a display, one or more sensors, one or more processors, and one or more non-transitory computer readable storage media having instructions stored thereon that, when executed by the one or more processors, cause the one or more processors to implement operations. The operations include receiving raw sensor data acquired from a patient from the one or more sensors; applying the raw sensor data to an input layer of a neural network to generate an input vector, wherein the input layer of the neural network orders the input vector such that real components and imaginary components of samples in the raw sensor data are adjacent; applying the input vector to a first convolutional layer of the neural network to generate a filtered input vector; applying the filtered input vector to at least one fully connected layer of the neural network to generate a matrix; applying the matrix to at least one additional convolutional layer of the neural network different from the first convolutional layer to generate a medical image of the patient; and causing the display to display the medial image of the patient for clinical analysis.

BRIEF DESCRIPTION OF THE DRAWINGS

FIG. 15A shows a second series of example medical images that are generated using different approaches and their associated errors, in accordance with some aspects of the disclosure.

FIG. 17 shows a table illustrating error data associated with different approaches to generating medial images, in accordance with some aspects of the disclosure.

DETAILED DESCRIPTION

Imaging is important to a wide range of industries and activities. From space exploration to oil exploration, imaging plays a key role in these endeavors. The modalities available for imaging are at least as diverse as the industries that employ them. For example, in the medical industry alone, a staggeringly large number of imaging modalities are employed in regular, clinical medicine. For example, to name but a few, magnetic resonance imaging (MM), computed tomography (CT) imaging, emission tomography imaging (including modalities such as positron emission tomography and single photon emission computed tomography), optical, x-ray fluoroscopy, and many, many others are utilized each day in modern medicine.

Regardless of the modality employed or the industry/application, reconstruction is a key process in any imaging process. In some settings, image reconstruction may be quite rudimentary or well settled. For example, image reconstruction for x-ray fluoroscopy generally includes translating attenuation values into contrast values in the digital image. Other modalities require much more complex reconstruction techniques.

In a computed tomography system, for example, an x-ray source projects a fan-shaped beam which is collimated to lie within an x-y plane of a Cartesian coordinate system, termed the "image plane." The x-ray beam passes through the object being imaged, such as a medical patient, and impinges upon an array of radiation detectors. The intensity of the transmitted radiation is dependent upon the attenuation of the x-ray beam by the object and each detector produces a separate electrical signal that is a measurement of the beam attenuation. The attenuation measurements from all the detectors are acquired separately to produce what is called the "transmission profile", "attenuation profile", or "projection". In x-ray fluoroscopy, this two-dimensional projection is translated into a single image.

The source and detector array in a CT system can be rotated on a gantry within the imaging plane and around the object so that the angle at which the x-ray beam intersects the object constantly changes. The transmission profile from the detector array at a given angle is referred to as a "view" and a "scan" of the object comprises a set of views made at different angular orientations during one revolution of the x-ray source and detector. In a 2D scan, data is processed to construct an image that corresponds to a two-dimensional slice taken through the object. The prevailing method for reconstructing an image from 2D data is referred to in the art as the filtered back projection technique. This image reconstruction process converts the attenuation measurements acquired during a scan into integers called "CT numbers" or "Hounsfield units", which are used to control the brightness of a corresponding pixel on a display.

Figure 1:
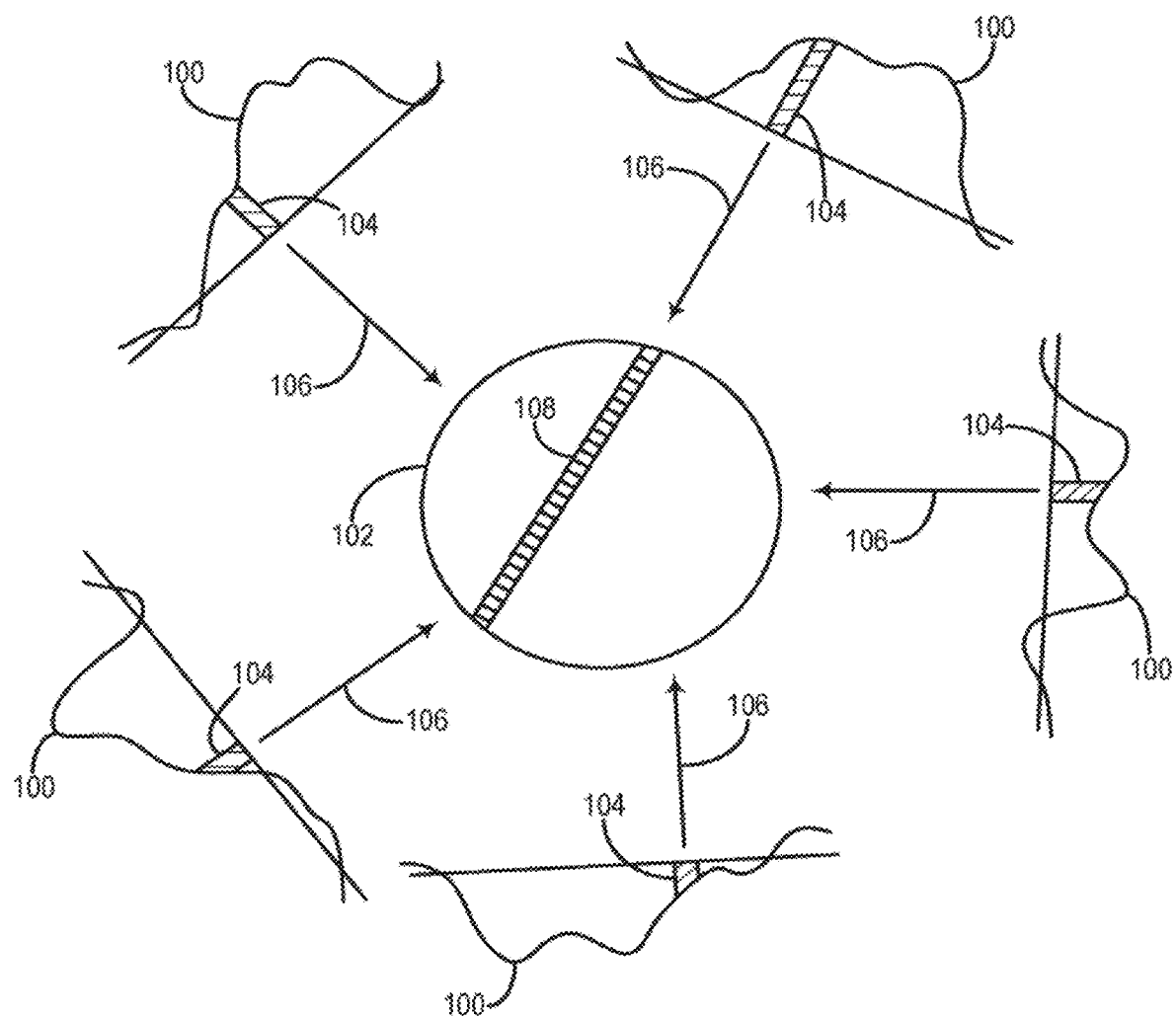
FIG. 1 shows a diagram illustrating filtered back projection image reconstruction using x-ray transmission profiles, in accordance with some aspects of the disclosure.

The filtered back projection image reconstruction method is the most common technique used to reconstruct CT images from acquired transmission profiles. As shown in FIG. 1, each acquired x-ray transmission profile 100 is back projected onto the field of view (FOV) 102 by projecting each ray sum 104 in the profile 100 through the FOV 102 along the same ray path that produced the ray sum 104 as indicated by arrows 106. In projecting each ray sum 104 in the FOV 102 we have no a priori knowledge of the subject and the assumption is made that the x-ray attenuation in the FOV 102 is homogeneous and that the ray sum should be distributed equally in each pixel through which the ray path passes. For example, a ray path 108 is illustrated in FIG. 1 for a single ray sum 104 in one transmission profile 100 and it passes through N pixels in the FOV 102. The attenuation value, P, of this ray sum 104 is divided up equally between these N pixels:

$$\mu_n = \frac{(P \times 1)}{N}$$

In the above equation, $\mu_n$ is the attenuation value distributed to the $n^{th}$ pixel in a ray path having N pixels. Clearly, the assumption that attenuation in the FOV 102 is homogeneous is not correct. However, as is well known in the art, if certain corrections are made to each transmission profile 100 and a sufficient number of profiles are acquired at a corresponding number of projection angles, the errors caused by this faulty assumption are minimized and image artifacts are suppressed. In a typical filtered back projection method of image reconstruction, anywhere from 400 to 1000 views are typically required to adequately suppress image artifacts in a 2D CT image.

MRI uses the nuclear magnetic resonance (NMR) phenomenon to produce images. When a substance such as human tissue is subjected to a uniform magnetic field (polarizing field B0), the individual magnetic moments of the spins in the tissue attempt to align with this polarizing field, but precess about it in random order at their characteristic Larmor frequency. If the substance, or tissue, is subjected to a magnetic field (excitation field B1) which is in the x-y plane and which is near the Larmor frequency, the net aligned moment, $M_Z$, may be rotated, or "tipped", into the x-y plane to produce a net transverse magnetic moment $M_{XY}$. A signal is emitted by the excited spins, and after the excitation signal B1 is terminated, this signal may be received and processed to form an image.

When utilizing these signals to produce images, magnetic field gradients ($G_X$, $G_Y$, and $G_Z$) are employed. Typically, the region to be imaged is scanned by a sequence of measurement cycles in which these gradients vary according to the particular localization method being used. The resulting set of received NMR signals, or k-space (e.g., frequency domain) samples, are digitized and processed to reconstruct the image using known reconstruction techniques.

Figure 2A:
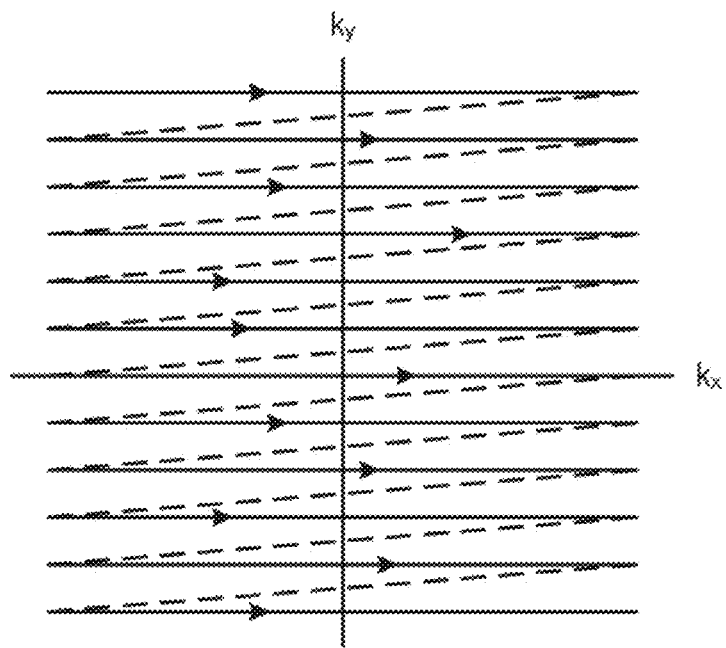
FIG. 2A shows a graph illustrating a Fourier imaging scan pattern that can be used to reconstruct k-space data, in accordance with some aspects of the disclosure.

Most commonly, when the k-space data is acquired using Cartesian sampling, the reconstruction of the data from k-space to the image space is achieved using a Fourier transform or any of a variety of reconstruction techniques that utilize a Fourier transform. Such a k-space sampling is illustrated in FIG. 2A. There are many, many variations on techniques for using the Fourier transform as part of a reconstruction process for k-space data sampled using a Cartesian or similar sampling strategy.

Figure 2B:
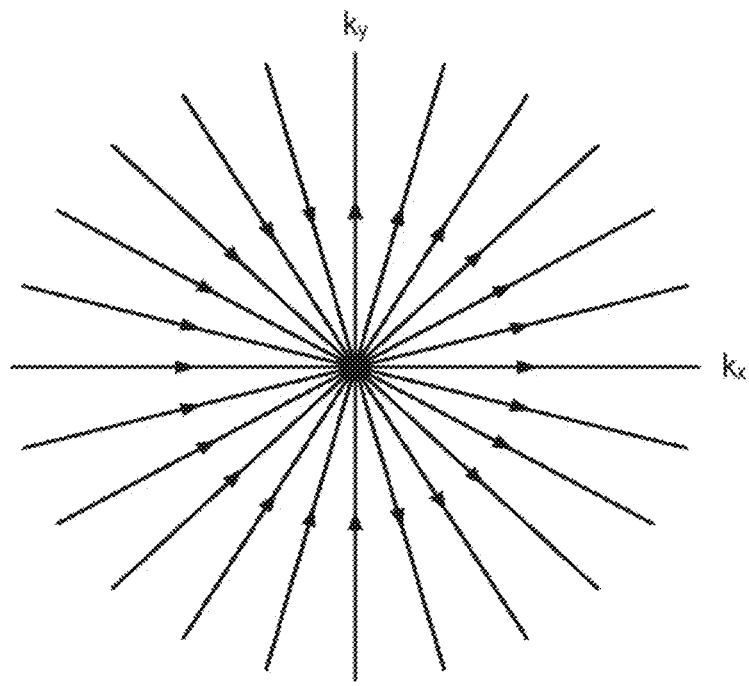
FIG. 2B shows a graph illustrating a projection reconstruction method that can sample k-space data as radial lines extending outward from the center of k-space, in accordance with some aspects of the disclosure.

Projection reconstruction methods have been known since the inception of magnetic resonance imaging. Rather than sampling k-space in a rectilinear, or Cartesian, scan pattern as is done in Fourier imaging and shown in FIG. 2A, projection reconstruction methods sample k-space data with a series of views that sample radial lines extending outward from the center of k-space as shown in FIG. 2B. The number of views needed to sample k-space determines the length of the scan and if an insufficient number of views are acquired, streak artifacts are produced in the reconstructed image.

In MRI the most common method is to re-grid the k-space samples (e.g., NMR data) from their locations on the radial sampling trajectories to a Cartesian grid. The image is then reconstructed by performing a 2D or 3D Fourier transformation of the re-gridded k-space samples. The second method for reconstructing an MR image is to transform the radial k-space projection views to Radon space by first Fourier transforming each projection view. An image is reconstructed from these signal projections by filtering and back projecting them into the field of view. As is well known in the art, if the acquired signal projections are insufficient in number to satisfy the Nyquist sampling theorem, streak artifacts are produced in the reconstructed image.

Depending on the technique used, many MR scans currently used to produce medical images require many minutes to acquire the necessary data. The reduction of this scan time is an important consideration, since reduced scan time increases patient throughput, improves patient comfort, and improves image quality by reducing motion artifacts. Many different strategies have been developed to shorten the scan time.

One such strategy is referred to generally as "parallel imaging". Parallel imaging techniques use spatial information from arrays of RF receiver coils to substitute for the encoding that would otherwise have to be obtained in a sequential fashion using RF pulses and field gradients (such as phase and frequency encoding). Each of the spatially independent receiver coils of the array carries certain spatial information and has a different sensitivity profile. This information is utilized in order to achieve a complete location encoding of the received MR signals by a combination of the simultaneously acquired data received from the separate coils. Specifically, parallel imaging techniques under sample k-space by reducing the number of acquired phase-encoded k-space sampling lines while keeping the maximal extent covered in k-space fixed. The combination of the separate MR signals produced by the separate receiver coils enables a reduction of the acquisition time required for an image (in comparison to conventional k-space data acquisition) by a factor that in the most favorable case equals the number of the receiver coils. Thus, the use of multiple receiver coils acts to multiply imaging speed, without increasing gradient switching rates or RF power.

Two categories of such parallel imaging techniques that have been developed and applied to in vivo imaging are SENSE (SENSitivity Encoding) and SMASH (SiMultaneous Acquisition of Spatial Harmonics). With SENSE, the under sampled k-space data is first Fourier transformed to produce an aliased image from each coil, and then the aliased image signals are unfolded by a linear transformation of the superimposed pixel values. With SMASH, the omitted k-space lines are filled in or reconstructed prior to Fourier transformation, by constructing a weighted combination of neighboring lines acquired by the different receiver coils. SMASH requires that the spatial sensitivity of the coils be determined, and one way to do so is by "autocalibration" that entails the use of variable density k-space sampling.

The data acquisition methods are significantly different in the above exemplary imaging modalities. Namely, k-space is sampled to measure Fourier coefficients in MR data acquisitions, while line integrals are measured in x-ray CT data acquisitions. Despite this, the challenge in image reconstruction for both modalities, as well as many other imaging modalities, is common: reconstructing a high-quality image.

According to standard image reconstruction theories, in order to reconstruct an image without aliasing artifacts, the sampling rate employed to acquire image data must satisfy the so-called Nyquist criterion, which is set forth in the Nyquist-Shannon sampling theorem. Moreover, in standard image reconstruction theories, no specific prior information about the image is needed. On the other hand, when some prior information about the desired or target image is available and appropriately incorporated into the image reconstruction procedure, an image can be accurately reconstructed even if the Nyquist criterion is violated. For example, if one knows a desired, target image is circularly symmetric and spatially uniform, only one view of parallel-beam projections (i.e., one projection view) is needed to accurately reconstruct the linear attenuation coefficient of the object. As another example, if one knows that a desired, target image consists of only a single point, then only two orthogonal projections that intersect at said point are needed to accurately reconstruct the image point. Thus, if prior information is known about the desired target image, such as if the desired target image is a set of sparsely distributed points, it can be reconstructed from a set of data that was acquired in a manner that does not satisfy the Nyquist criterion. Put more generally, knowledge about the sparsity of the desired target image can be employed to relax the Nyquist criterion; however, it is a highly nontrivial task to generalize these arguments to formulate a rigorous image reconstruction theory.

The Nyquist criterion serves as one of the paramount foundations of the field of information science. However, it also plays a pivotal role in modern medical imaging modalities such as MIII and x-ray CT imaging. When the number of data samples acquired by an imaging system is less than the requirement imposed by the Nyquist criterion, artifacts appear in the reconstructed images. In general, such image artifacts include aliasing and streaking artifacts. In practice, the Nyquist criterion is often violated, whether intentionally or through unavoidable circumstances. For example, in order to shorten the data acquisition time in a time-resolved MR angiography study, under sampled projection reconstruction, or radial, acquisition methods are often intentionally introduced.

In contrast, under sampling is inevitable in four-dimensional cone beam CT (4D CBCT), such as when utilized in image-guided radiation therapy (IGRT). For example, in the case of IGRT, cone beam projection data are acquired over 10-15 respiratory cycles during a 60 second gantry rotation time. The acquired data is then retrospectively gated into 8-10 phases by synchronizing the respiratory signals with the data acquisition. After the respiratory gating, less than 100 cone beam projections are typically available to reconstruct images for each respiratory phase. Consequently, streaking artifacts are rampant in the reconstructed images for each respiratory phase. These under sampling artifacts pose a major challenge in 4D CBCT and limit the use of 4D CBCT in clinical practice.

Some image reconstruction methods have attempted to use prior or other information to overcome challenges to producing high-quality images. For example, one method called highly constrained back projection (HYPR) has been developed in which quality images can be reconstructed from far fewer projection signal profiles when a priori knowledge of the signal information is used in the reconstruction process. For example, signal information in an angiographic study may be known to include structures such as blood vessels. That being the case, when a back projection path passes through these structures a more accurate distribution of a signal sample in each pixel can be achieved by weighting the distribution as a function of the known signal information at that pixel location. In HYPR, for a back projection path having N pixels the highly constrained back projection may be expressed as follows:

$$S_n = \frac{(P \times C_n)}{\sum_{n=1}^{N} C_n}$$

In the above equation, $S_n$ is the back projected signal magnitude at a pixel n in an image frame being reconstructed, P is the signal sample value in the projection profile being back projected, and $C_n$ is the signal value of an a priori composite image at the $n^{th}$ pixel along the back projection path. The composite image is reconstructed from data acquired during the scan, and may include that used to reconstruct the given image frame as well as other acquired image data that depicts the structures in the field of view. The numerator in the equation above, $(P \times C_n)$, weights each pixel using the corresponding signal value in the composite image and the denominator, $$\sum_{n=1}^{N} C_n,$$

normalizes the value so that all back projected signal samples reflect the projection sums for the image frame and are not multiplied by the sum of the composite image.

Regardless of the imaging modality or the data type acquired, all reconstruction techniques are fundamentally based on a few principles. First, a known data sampling is performed to yield a set of data of known characteristics. Then, based on the known data sampling technique and the known characteristics of the data set, an appropriate reconstruction technique is applied that will transform the raw set of data into an image. Thus, a known reconstruction technique matched to the underlying data is applied that serves to transform the raw data from a first domain in which it was acquired to a second domain where it can be understood as an image.

For example, in CT, the data is acquired as Hounsfield units that are transformed using filtered back projection or another technique into pixels with associated contrast values in an image. In MR, the data is acquired as k-space or frequency domain data that is transformed using, typically a type of Fourier transform, into the image domain (e.g., a spatial domain in which the arrangement and relationship among different pixel values are expressed) to generate an image. Other imaging modalities follow this exact or similar process. For example, PET imaging uses the filtered back projection technique.

Despite the success of this paradigm in medical and non-medical imaging applications, they suffer from regular and extensive shortcomings. Case in point, the Nyquist criterion is a fundamental tenant of imaging that, when not observed, often requires extensive efforts to buttress the applicable reconstruction technique with additional compensations to overcome the fact that the resulting images, without such compensation, would suffer from artifacts that reduce the value of the images. Thus, in the patent literature alone, there are thousands of examples of small changes, additions, or variations on the fundamental reconstruction techniques.

The present disclosure provides in some aspects systems, methods, and media that can transform raw data into an image and, thereby, serve as a reconstruction technique, but without the need for the reconstruction technique being predesigned to compensate for anticipated data acquisition characteristics, including shortcomings in the data (such as under sampling). Furthermore, the present disclosure provides in some aspects systems, methods, and media that can provide feedback that informs the data acquisition techniques that can be used in the future. That is, the reconstruction process is not dictated by the data acquisition process, but rather data reconstruction can be performed irrespective of data acquisition and, instead, serve to inform future data acquisitions to further improve reconstructed images.

The present disclosure also provides in some aspects systems, methods, and media for transforming data sets acquired in a first domain into a data set in a second domain using aggregated preferred results in the second domain as a guide for informing the domain transform or reconstruction process. This stands in contrast to traditional domain transform or reconstruction techniques that dictate the way in which the data must be acquired in the first domain so that the domain transform or reconstruction technique can deliver results in the second domain that are desirable. That is, in the case of projections acquired through k-space in MRI, one typically re-grids the data to allow a Fourier transform to be performed. In this way, the preconception of the data by the reconstruction technique necessitates that the data be presented (in both form and substance—such as sampling density) in a predetermined manner that will yield desirable images when transformed to the image domain. The systems, methods, and media described herein may not be limited in this manner. A framework is provided that can be leveraged to create images or transform data from one domain to another without a preconceived constraint on the data acquired or to be acquired.

For example, a data-driven manifold learning construct can be used as a generalized image reconstruction technique to transform raw sensor to another domain or, in the case of imaging, transform image data into images, without human-devised, acquisition-specific mathematical transforms. In a non-limiting context, this construct or framework may be referred to herein as AUTOMAP (AUtomated TransfOrm by Manifold Approximation) or in some cases as a deep reconstruction network (DRN).

By not constraining the image reconstruction or domain transfer problem to human-devised, acquisition-specific transforms, new signal domains beyond conventional representations (e.g., k-space/Fourier space, O-space, Radon, etc.) can be used acquire data. Reinforcement learning can be used to automatically program novel methods for data acquisition. As one non-limiting example, AUTOMAP can be used to design new pulse sequences for MRI. Likewise, the data acquisition itself need not be constrained to known domains. The automated acquisition and automated reconstruction stages can be trained in tandem to produce optimal imaging protocols and resultant images.

Accordingly, the systems, methods, and media described herein can be used in any of a variety of setting where one looks to transform data from one domain to another domain and/or develop and devise data acquisition strategies that yield improved results by analyzing the desired ends to the data acquisition. For example, beyond the non-limiting examples provided herein, the systems and methods of the present disclosure can be extended to other imaging modalities, such as optical (e.g., optical coherence tomography, speckle imaging, and the like) and even non-imaging applications, such as general data processing.

Moreover, the systems, methods, and media described herein are not limited to applications where a domain transform is necessary or advantageous to yield an image or improved image. This and other points will be made clear with respect to the following description. However, before turning to some more specific aspects of the present disclosure, some non-limiting examples of operational environments in which aspects of the present disclosure can be implemented (e.g., imaging systems) are provided.

Figure 3A:
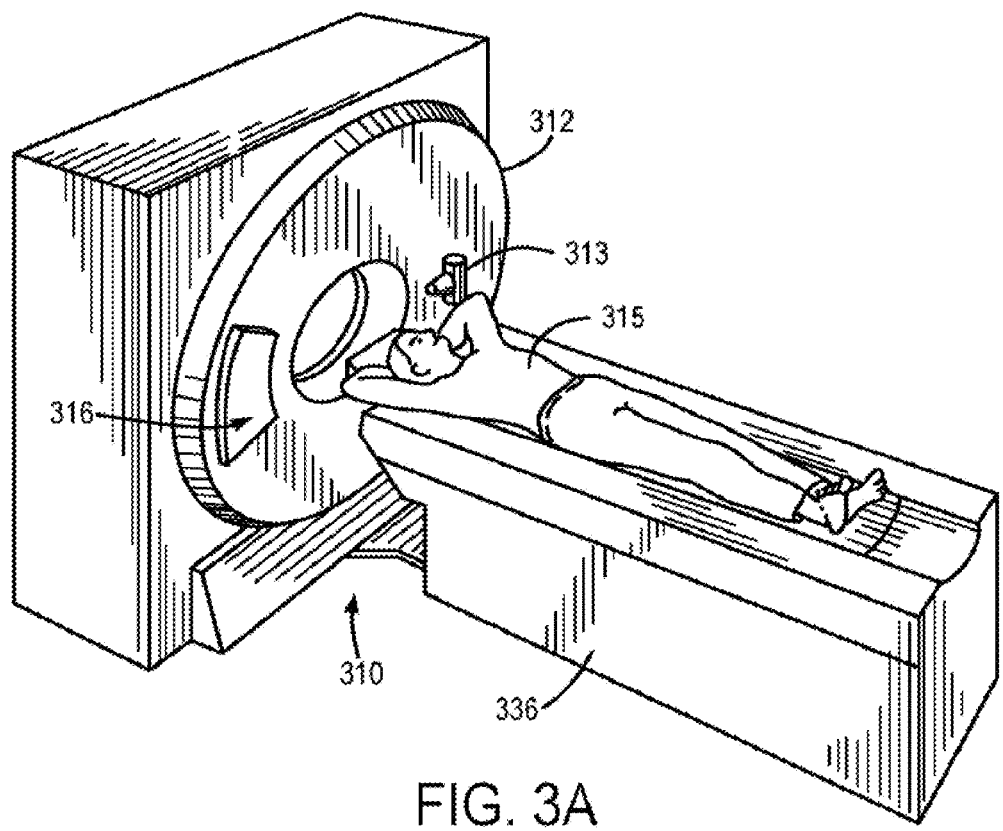
FIG. 3A shows an illustration of an example x-ray computed tomography (CT) imaging system, in accordance with some aspects of the disclosure.
Figure 3B:
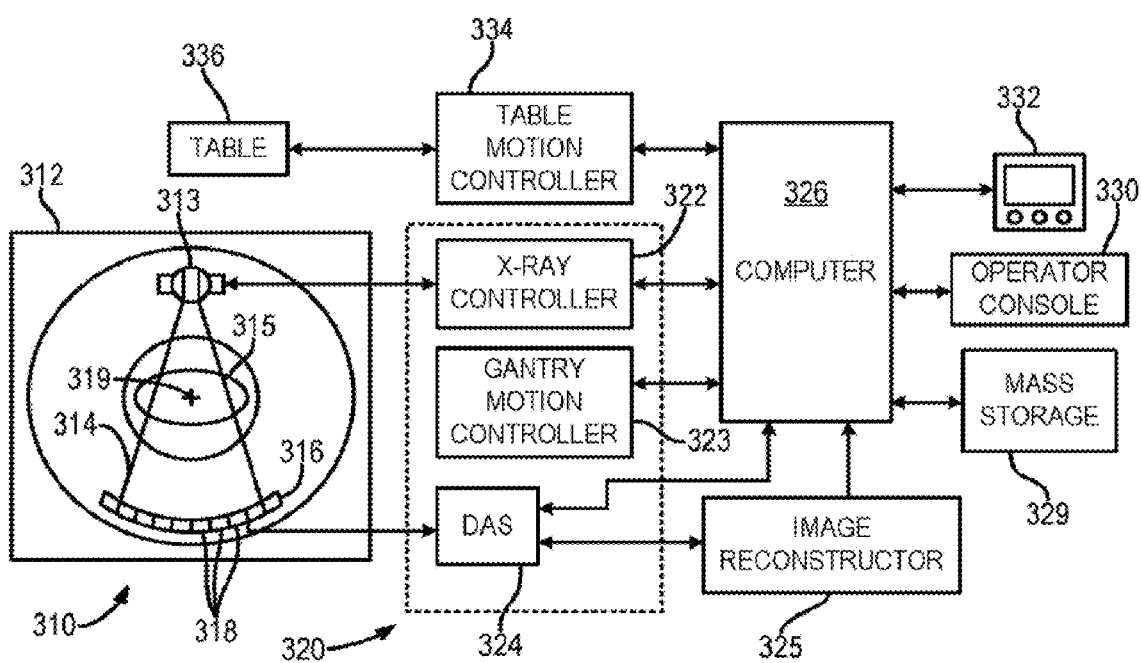
FIG. 3B shows a system diagram of the example x-ray CT imaging system of FIG. 3A, in accordance with some aspects of the disclosure.

Referring to FIG. 3A and FIG. 3B, specifically, an x-ray computed tomography (CT) imaging system 310 is shown that includes a gantry 312 representative of a "third generation" CT scanner. Gantry 312 has an x-ray source 313 that projects a fan beam, or cone beam, of x-rays 314 toward a detector array 316 on the opposite side of the gantry. The detector array 316 is formed by a number of detector elements 318 which together sense the projected x-rays that pass through a medical patient 315. Each detector element 318 produces an electrical signal that represents the intensity of an impinging x-ray beam and hence the attenuation of the beam as it passes through the patient. As will be described, this acquired attenuation data of a CT system 310 can be referred to as "sensor data". In the case of CT imaging, such data is typically in Radon space and measured in Hounsfield units. In this way, such sensor data can be referred to as being acquired in a "sensor domain". In the case of CT imaging and its respective sensor domain, the sensor data must be transformed to an image domain, such as by using filtered back projection, to yield a reconstructed image. However, as will be described, constraining reconstruction or acquisition based on such traditional tools for domain transfer and their inherent limitations is not necessary. Thus, as will be explained, breaking from this traditional paradigm of CT image reconstruction can yield, in accordance with the present disclosure, superior images.

During a scan to acquire x-ray projection data, the gantry 312 and the components mounted thereon rotate about a center of rotation 319 located within the patient 315. The rotation of the gantry and the operation of the x-ray source 313 are governed by a control mechanism 320 of the CT system. The control mechanism 320 includes an x-ray controller 322 that provides power and timing signals to the x-ray source 313 and a gantry motor controller 323 that controls the rotational speed and position of the gantry 312. A data acquisition system (DAS) 324 in the control mechanism 320 samples analog data from detector elements 318 and converts the data to digital signals for subsequent processing. An image reconstructor 325, receives sampled and digitized x-ray data from the DAS 324 and performs high speed image reconstruction. The reconstructed image is applied as an input to a computer 326 which stores the image in a mass storage device 328.

The computer 326 also receives commands and scanning parameters from an operator via console 330 that has a keyboard. An associated display 332 allows the operator to observe the reconstructed image and other data from the computer 326. The operator supplied commands and parameters are used by the computer 326 to provide control signals and information to the DAS 324, the x-ray controller 322 and the gantry motor controller 323. In addition, computer 326 operates a table motor controller 334 which controls a motorized table 336 to position the patient 315 in the gantry 312.

Figure 4A:
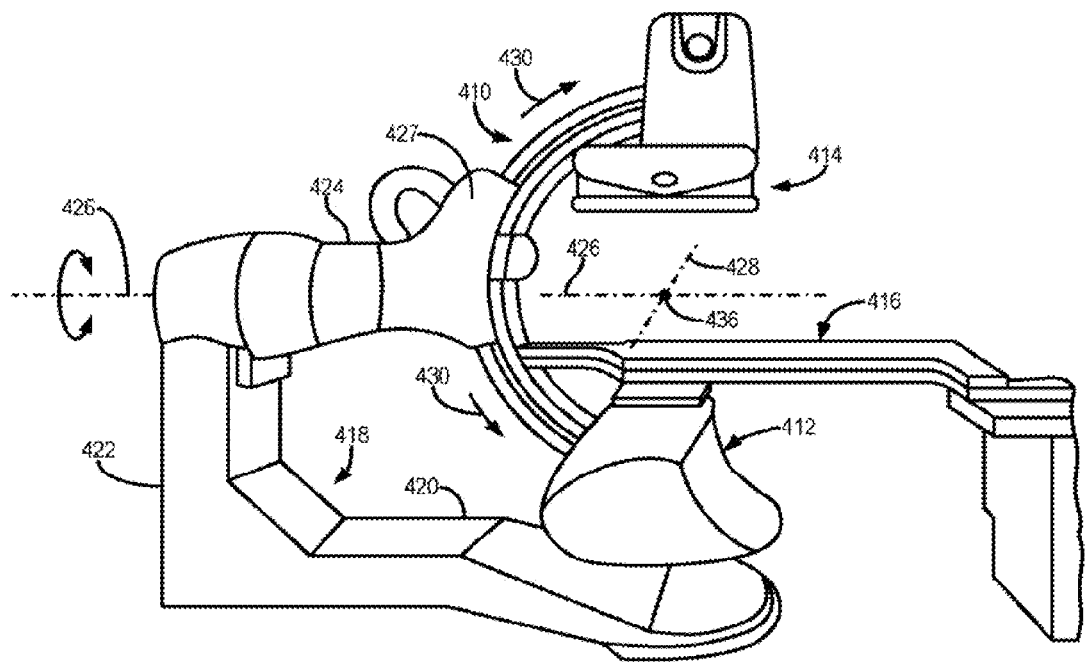
FIG. 4A shows an illustration of another example x-ray CT imaging system, in accordance with some aspects of the disclosure.
Figure 4B:
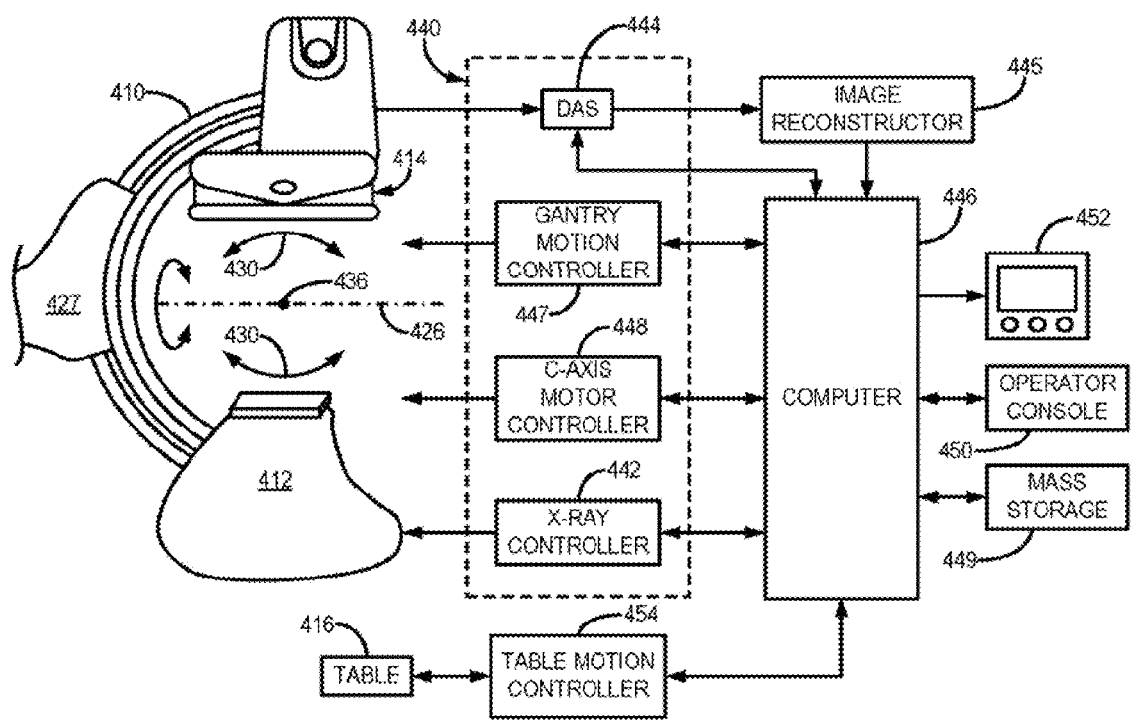
FIG. 4B shows a system diagram of the example x-ray CT imaging system of FIG. 4A, in accordance with some aspects of the disclosure.

Referring to FIG. 4A and FIG. 4B, an example x-ray system is shown that is designed for use in connection with interventional procedures. It is characterized by a gantry having a C-arm 410 which carries an x-ray source assembly 412 on one of its ends and an x-ray detector array assembly 414 at its other end. Similar to the above-described CT system 310, the data acquired by the C-arm system illustrated in FIGS. 4A and 4B can be referred to as "sensor data", in this case, typically, acquired in Radon space and measured in Hounsfield units. Again, such sensor data must be transformed to an image domain, such as by using filtered back projection, to yield a reconstructed image.

The gantry enables the x-ray source 412 and detector 414 to be oriented in different positions and angles around a patient disposed on a table 416, while enabling a physician access to the patient. The gantry includes an L-shaped pedestal 418 which has a horizontal leg 420 that extends beneath the table 416 and a vertical leg 422 that extends upward at the end of the horizontal leg 420 that is spaced from of the table 416. A support arm 424 is rotatably fastened to the upper end of vertical leg 422 for rotation about a horizontal pivot axis 426. The pivot axis 426 is aligned with the centerline of the table 416 and the arm 424 extends radially outward from the pivot axis 426 to support a C-arm drive assembly 427 on its outer end. The C-arm 410 is slidably fastened to the drive assembly 427 and can be coupled to a drive motor which slides the C-arm 410 to revolve it about a C-axis 428 as indicated by arrows 430. The pivot axis 426 and C-axis 428 intersect each other at an isocenter 436 located above the table 416 and they are perpendicular to each other.

The x-ray source assembly 412 is mounted to one end of the C-arm 410 and the detector array assembly 414 is mounted to its other end. As will be discussed in more detail below, the x-ray source 412 emits a cone beam of x-rays which are directed at the detector array 414. Both assemblies 412 and 414 extend radially inward to the pivot axis 426 such that the center ray of this cone beam passes through the system isocenter 436. The center ray of the cone beam can thus be rotated about the system isocenter around either the pivot axis 426 or the C-axis 428, or both during the acquisition of x-ray attenuation data from a subject placed on the table 416.

Referring particularly to FIG. 4B, the rotation of the assemblies 412 and 414 and the operation of the x-ray source 432 are governed by a control mechanism 440 of the CT system. The control mechanism 440 includes an x-ray controller 442 that provides power and timing signals to the x-ray source 432. A data acquisition system (DAS) 444 in the control mechanism 440 samples data from detector elements 438 and passes the data to an image reconstructor 445. The image reconstructor 445, receives digitized x-ray data from the DAS 444 and performs high speed image reconstruction according to the methods of the present invention. The reconstructed image is applied as an input to a computer 446 which stores the image in a mass storage device 449 or processes the image further.

The control mechanism 440 also includes pivot motor controller 447 and a C-axis motor controller 448. In response to motion commands from the computer 446 the motor controllers 447 and 448 provide power to motors in the x-ray system that produce the rotations about respective pivot axis 426 and C-axis 428. A program executed by the computer 446 generates motion commands to the motor drives 447 and 448 to move the assemblies 412 and 414 in a prescribed scan path.

The computer 446 also receives commands and scanning parameters from an operator via console 450 that has a keyboard and other manually operable controls. An associated cathode ray tube display 452 allows the operator to observe the reconstructed image and other data from the computer 446. The operator supplied commands are used by the computer 446 under the direction of stored programs to provide control signals and information to the DAS 444, the x-ray controller 442 and the motor controllers 447 and 448. In addition, computer 446 operates a table motor controller 454 which controls the motorized table 416 to position the patient with respect to the system isocenter 436.

Figure 5:
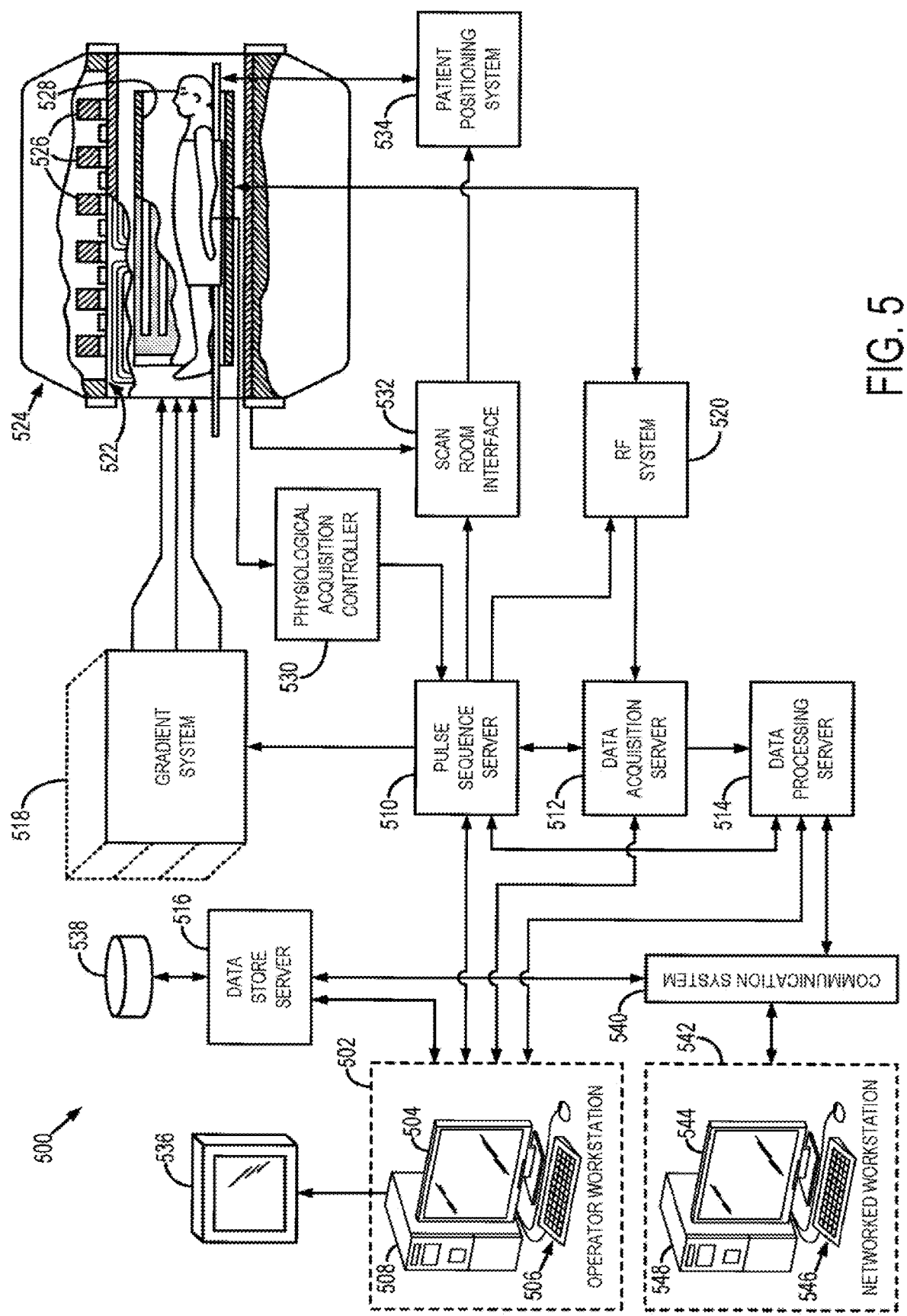
FIG. 5 shows a diagram of an example magnetic resonance imaging (MM) system, in accordance with some aspects of the disclosure.

Referring to FIG. 5, an example of an MRI system 500 is illustrated. The MRI system 500 includes a workstation 502 having a display 504 and a keyboard 506. The workstation 502 includes a processor 508 that is commercially available to run a commercially available operating system. The workstation 502 provides the operator interface that enables scan prescriptions to be entered into the MRI system 500. The workstation 502 is coupled to four servers: a pulse sequence server 510; a data acquisition server 512; a data processing server 514; and a data store server 516. The workstation 502 and each of the servers 510, 512, 514, and 516 are communicatively connected to communicate with each other.

The pulse sequence server 510 functions in response to instructions downloaded from the workstation 502 to operate a gradient system 518 and a radiofrequency (RF) system 520. Gradient waveforms necessary to perform the prescribed scan are produced and applied to the gradient system 518, which excites gradient coils in an assembly 522 to produce the magnetic field gradients $G_x$, $G_y$, and $G_z$ used for position encoding MR signals. The gradient coil assembly 522 forms part of a magnet assembly 524 that includes a polarizing magnet 126 and a whole-body RF coil 528 and/or local coil.

RF excitation waveforms are applied to the RF coil 528, or a separate local coil, such as a head coil, by the RF system 520 to perform the prescribed magnetic resonance pulse sequence. Responsive MR signals detected by the RF coil 528, or a separate local coil, are received by the RF system 520, amplified, demodulated, filtered, and digitized under direction of commands produced by the pulse sequence server 510. The RF system 520 includes an RF transmitter for producing a wide variety of RF pulses used in MR pulse sequences. The RF transmitter is responsive to the scan prescription and direction from the pulse sequence server 510 to produce RF pulses of the desired frequency, phase, and pulse amplitude waveform. The generated RF pulses may be applied to the whole-body RF coil 528 or to one or more local coils or coil arrays.

The RF system 520 also includes one or more RF receiver channels. Each RF receiver channel includes an RF preamplifier that amplifies the MR signal received by the coil 528 to which it is connected, and a detector that detects and digitizes the quadrature components of the received MR signal. The magnitude of the received MR signal may thus be determined at any sampled point by the square root of the sum of the squares of the I and Q components:

$$M=\sqrt{I^2+Q^2}$$

Also, the phase of the received MR signal may also be determined using the equation:

$$\varphi = \tan^{-1}\left(\frac{Q}{I}\right)$$

In the case of an MRI system 500, these acquired RF signals are sampled in "k-space", which is a frequency domain. Thus, the MRI system 500 acquires "sensor data" in the frequency domain, which represents the "sensor domain" for MR or NMR imaging. Such MR sensor data can then be transformed to an image domain to yield a reconstructed image, which can be achieved via a Fourier transform or projection reconstruction technique. However, as will be described, constraining reconstruction or acquisition based on such tools for domain transfer and their inherent limitations may not be necessary. Thus, breaking from this traditional paradigm of MR image reconstruction can yield superior images.

The pulse sequence server 510 also optionally receives patient data from a physiological acquisition controller 530. The controller 530 receives signals from a number of different sensors connected to the subject to be scanned, such as electrocardiograph (ECG) signals from electrodes, or respiratory signals from a bellows or other respiratory monitoring device. Such signals are typically used by the pulse sequence server 510 to synchronize, or "gate", the performance of the scan with the subject's heartbeat or respiration. The pulse sequence server 510 also connects to a scan room interface circuit 532 that receives signals from various sensors associated with the condition of the patient and the magnet system. A patient positioning system 532 may be included.

The digitized MR signal samples produced by the RF system 520 are received by the data acquisition server 512. The data acquisition server 512 operates in response to instructions downloaded from the workstation 502 to receive the real-time MR data and provide buffer storage, such that no data is lost by data overrun. In some scans, the data acquisition server 512 does little more than pass the acquired MR data to the data processor server 514. However, in scans that require information derived from acquired MR data to control the further performance of the scan, the data acquisition server 512 is programmed to produce such information and convey it to the pulse sequence server 510. For example, during pre-scans, MR data is acquired and used to calibrate the pulse sequence performed by the pulse sequence server 510. Also, navigator signals may be acquired during a scan and used to adjust the operating parameters of the RF system 520 or the gradient system 518, or to control the view order in which k-space data (e.g., frequency domain data) is sampled. In all these examples, the data acquisition server 512 acquires MR data and processes it in real-time to produce information that is used to control the scan.

The data processing server 514 receives MR data from the data acquisition server 512 and processes it in accordance with instructions downloaded from the workstation 502. Such processing may include, for example: Fourier transformation of raw k-space MR data to produce two or three-dimensional images; the application of filters to a reconstructed image; the performance of a back projection image reconstruction of acquired MR data; the generation of functional MR images; and the calculation of motion or flow images.

Images reconstructed by the data processing server 514 are conveyed back to the workstation 502 where they are stored. Real-time images are stored in a data base memory cache, from which they may be output to operator display 504 or a display 536 that is located near the magnet assembly 524 for use by attending physicians. Batch mode images or selected real time images are stored in a host database on disc storage 538. When such images have been reconstructed and transferred to storage, the data processing server 514 notifies the data store server 516 on the workstation 502. The workstation 502 may be used by an operator to archive the images, produce films, or send the images via a network or communication system 540 to other facilities that may include other networked workstations 542.

The communication system 540 and networked workstation 542 may represent any of the variety of local and remote computer systems that may be included within a given imaging facility including the system 500 or other, remote location that can communicate with the system 500. In this regard, the networked workstation 542 may be functionally and capably similar or equivalent to the operator workstation 502, despite being located remotely and communicating over the communication system 540. As such, the networked workstation 542 may have a display 544 and a keyboard 546. The networked workstation 542 includes a processor 548 that is commercially available to run a commercially available operating system. The networked workstation 542 may be able to provide the operator interface that enables scan prescriptions to be entered into the MRI system 500.

Figure 6:
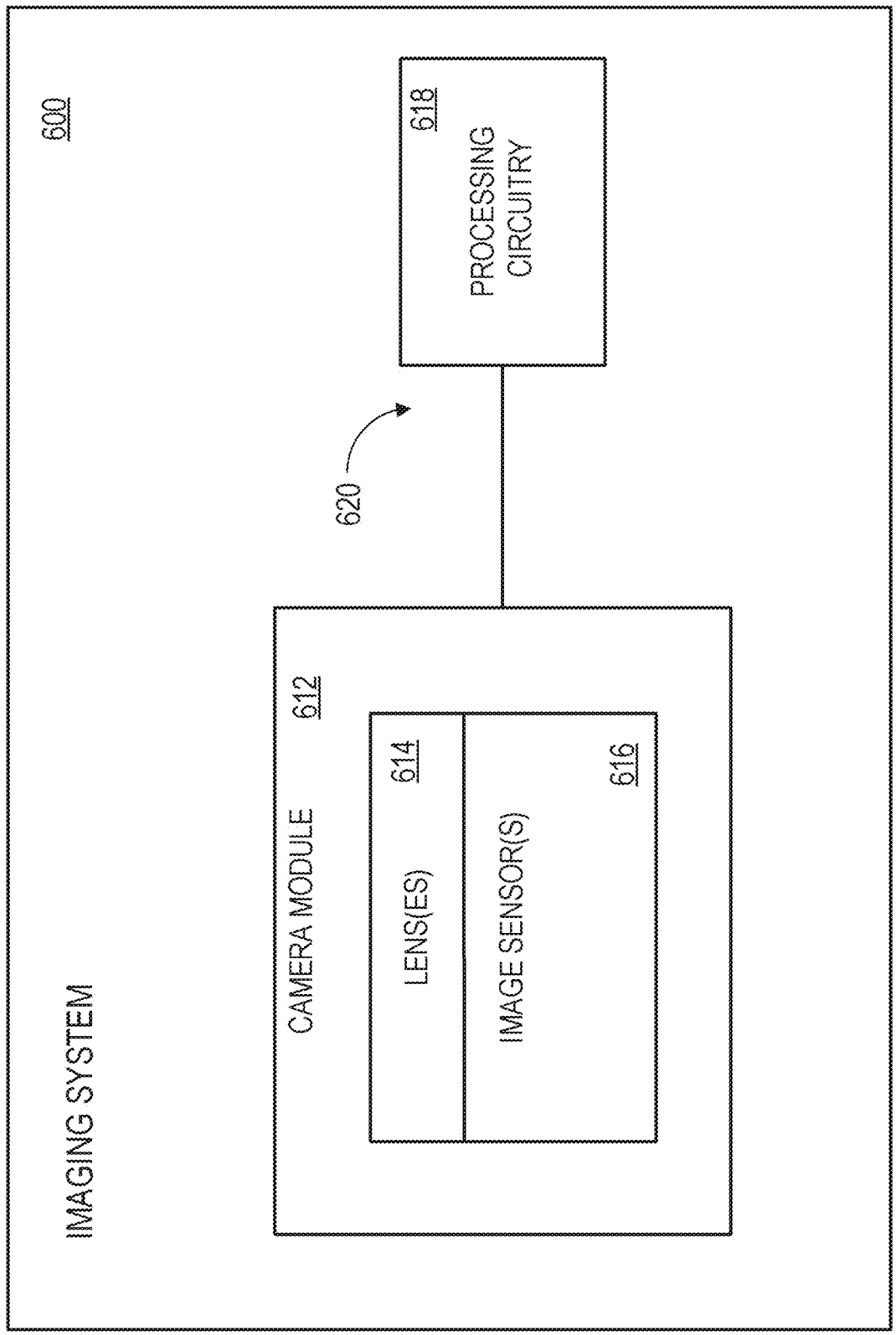
FIG. 6 shows a diagram of an example imaging system that uses one or more image sensors to optically capture images, in accordance with some aspects of the disclosure.

FIG. 6 shows an example imaging system 600 that uses one or more image sensors to capture images and that includes processing circuitry configured to execute an AUTOMAP image reconstruction algorithm such as detailed further below. The imaging system 600 may be a portable imaging system such as a camera, a cellular telephone, a video camera, or any other imaging device that captures digital image data. A camera module 612 may be used to convert incoming light into digital image data. The camera module 612 includes one or more lenses 614 and one or more corresponding image sensors 616. In some embodiments, the lens 614 may be part of an array of lenses and image sensor 616 may be part of an image sensor array.

Processing circuitry 618 may include one or more integrated circuits (e.g., image processing circuits, microprocessors, storage devices such as random-access memory and non-volatile memory, etc.) and may be connected via in input 620 to the camera module 612 and/or that form part of the camera module 612 (e.g., circuits that form part of an integrated circuit that includes the image sensor 616 or an integrated circuit within the camera module 612 that is associated with the image sensor 616). Image data that has been captured and processed by the camera module 612 may, if desired, be further processed and stored using the processing circuitry 618. Processed image data may, if desired, be provided to external equipment, such as a computer or other electronic device, using wired and/or wireless communication paths coupled to the processing circuitry 618. For example, the processing circuitry 618 may include a field programmable gate array (FPGA) or an application specific integrated circuit (ASIC), with which the AUTOMAP data-driven manifold learning processes may be performed in order to execute generalized image reconstruction techniques to transform raw data (e.g., pixel voltages) generated by the image sensor 616 into images in the image domain (e.g., a spatial domain in which the arrangement and relationship among different pixel values are expressed) without the use of human-devised acquisition-specific mathematical functions.

For example, an array of photo-sensitive pixels within the image sensor 616 may generate an array of pixel voltages corresponding to a captured image when exposed to light. This array of pixel voltages may be transformed into visual representations of the captured image in the image domain using a learned (e.g., trained) AUTOMAP image reconstruction process executed by the processing circuitry 618. For example, a neural network may be used to transform digital voltages output by analog-to-digital converter (ADC) circuitry (e.g., that processes the outputs of the pixels of the image sensor 616) to the image domain.

Digital photography and cinematography performed in low-light conditions may result in low-quality images and videos due to image sensor non-idealities (e.g., thermal noise of CCD and CMOS image sensors or read-out noise of on-chip amplifiers in the image sensor) when using traditional image processing techniques. By using learned AUTOMAP image reconstruction in place of traditional image processing techniques, image sensor defects may be automatically compensated for and, because learned image reconstruction may be robust to corruptive channel noise such as additive white Gaussian noise, signal-to-noise ratio (SNR) for the image may be comparatively improved, especially when the learned image reconstruction is trained using real-world representative data (images).

Figure 7:
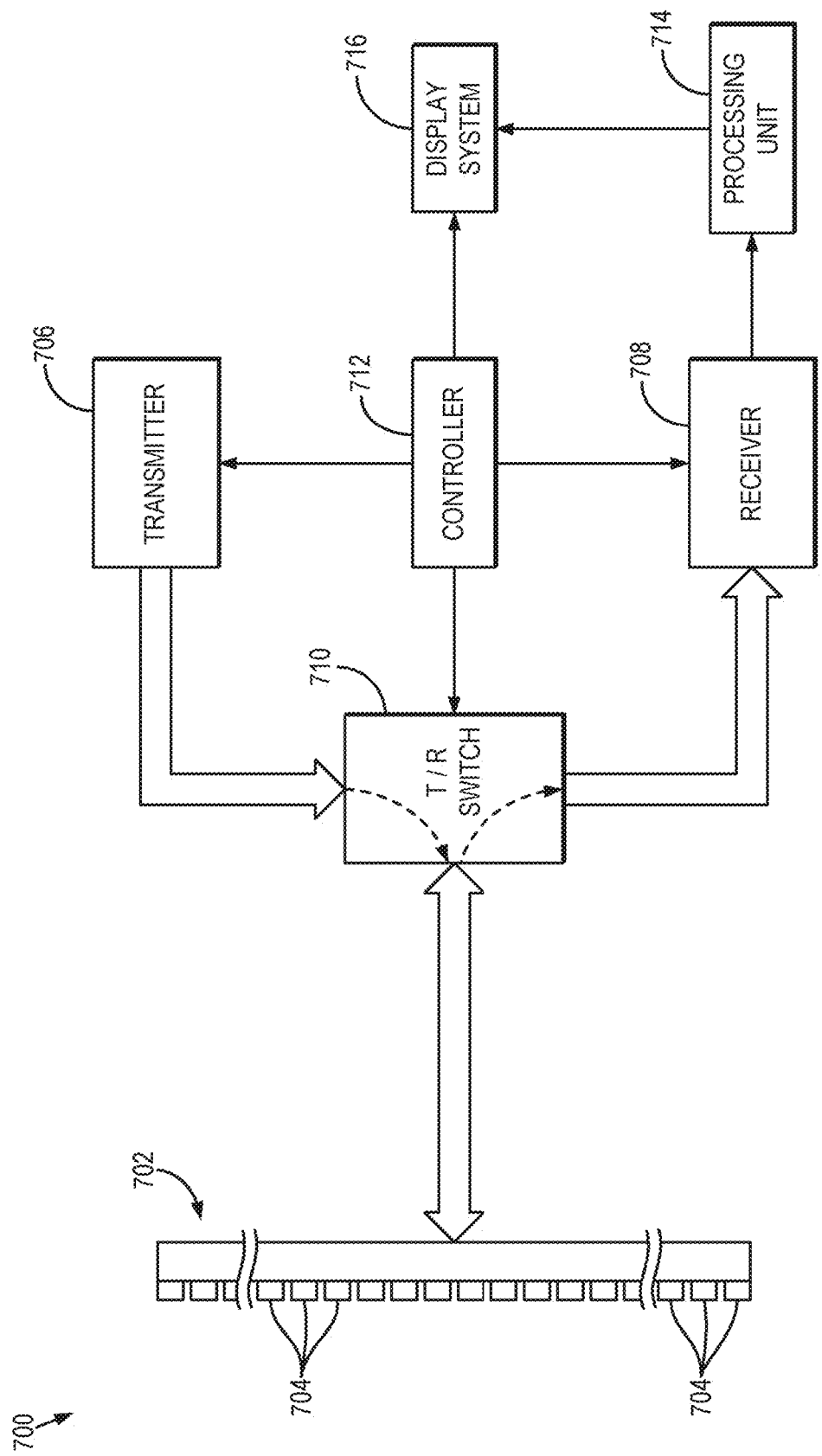
FIG. 7 shows a diagram of an example ultrasound system, in accordance with some aspects of the disclosure.

FIG. 7 shows an example ultrasound system 700 that can implement the methods described in the present disclosure. The ultrasound system 700 includes a transducer array 702 that includes a plurality of separately driven transducer elements 704. The transducer array 702 can include any suitable ultrasound transducer array, including linear arrays, curved arrays, phased arrays, and so on. Similarly, the transducer array 702 can include a 1D transducer, a 1.5D transducer, a 1.75D transducer, a 2D transducer, a 3D transducer, and so on.

When energized by a transmitter 706, a given transducer element 704 produces a burst of ultrasonic energy. The ultrasonic energy reflected back to the transducer array 702 (e.g., an echo) from the object or subject under study is converted to an electrical signal (e.g., an echo signal) by each transducer element 704 and can be applied separately to a receiver 708 through a set of switches 710. The transmitter 706, receiver 708, and switches 710 are operated under the control of a controller 712, which may include one or more processors. As one example, the controller 712 can include a computer system.

The transmitter 706 can be programmed to transmit unfocused or focused ultrasound waves. In some configurations, the transmitter 706 can also be programmed to transmit diverged waves, spherical waves, cylindrical waves, plane waves, or combinations thereof. Furthermore, the transmitter 706 can be programmed to transmit spatially or temporally encoded pulses. The receiver 708 can be programmed to implement a suitable detection sequence for the imaging task at hand. In some embodiments, the detection sequence can include one or more of line-by-line scanning, compounding plane wave imaging, synthetic aperture imaging, and compounding diverging beam imaging.

In some configurations, the transmitter 706 and the receiver 708 can be programmed to implement a high frame rate. For instance, a frame rate associated with an acquisition pulse repetition frequency ("PRF") of at least 100 Hz can be implemented. In some configurations, the ultrasound system 700 can sample and store at least one hundred ensembles of echo signals in the temporal direction. The controller 712 can be programmed to design an imaging sequence. In some examples, the controller 712 receives user inputs defining various factors used in the design of the imaging sequence.

A scan can be performed by setting the switches 710 to their transmit position, thereby directing the transmitter 706 to be turned on momentarily to energize transducer elements 704 during a single transmission event according to the designed imaging sequence. The switches 710 can then be set to their receive position and the subsequent echo signals produced by the transducer elements 704 in response to one or more detected echoes are measured and applied to the receiver 708. The separate echo signals from the transducer elements 704 can be combined in the receiver 708 to produce a single echo signal. The echo signals are communicated to a processing unit 714, which may be implemented by a hardware processor and memory, to process echo signals or images generated from echo signals. As an example, the processing unit 714 can implement AUTOMAP image reconstruction, including realizing a neural network (e.g., the models 900, 1000, 1300 detailed below) for transforming the echo signals (e.g., raw data in the sensor domain in which the ultrasound system 700 operates) into a visual representation (e.g., an image in the image domain) of the object or subject under study, or of a portion thereof, using the methods described in the present disclosure. Images produced from the echo signals by the processing unit 714 can be displayed on a display system 716.

Figure 8:
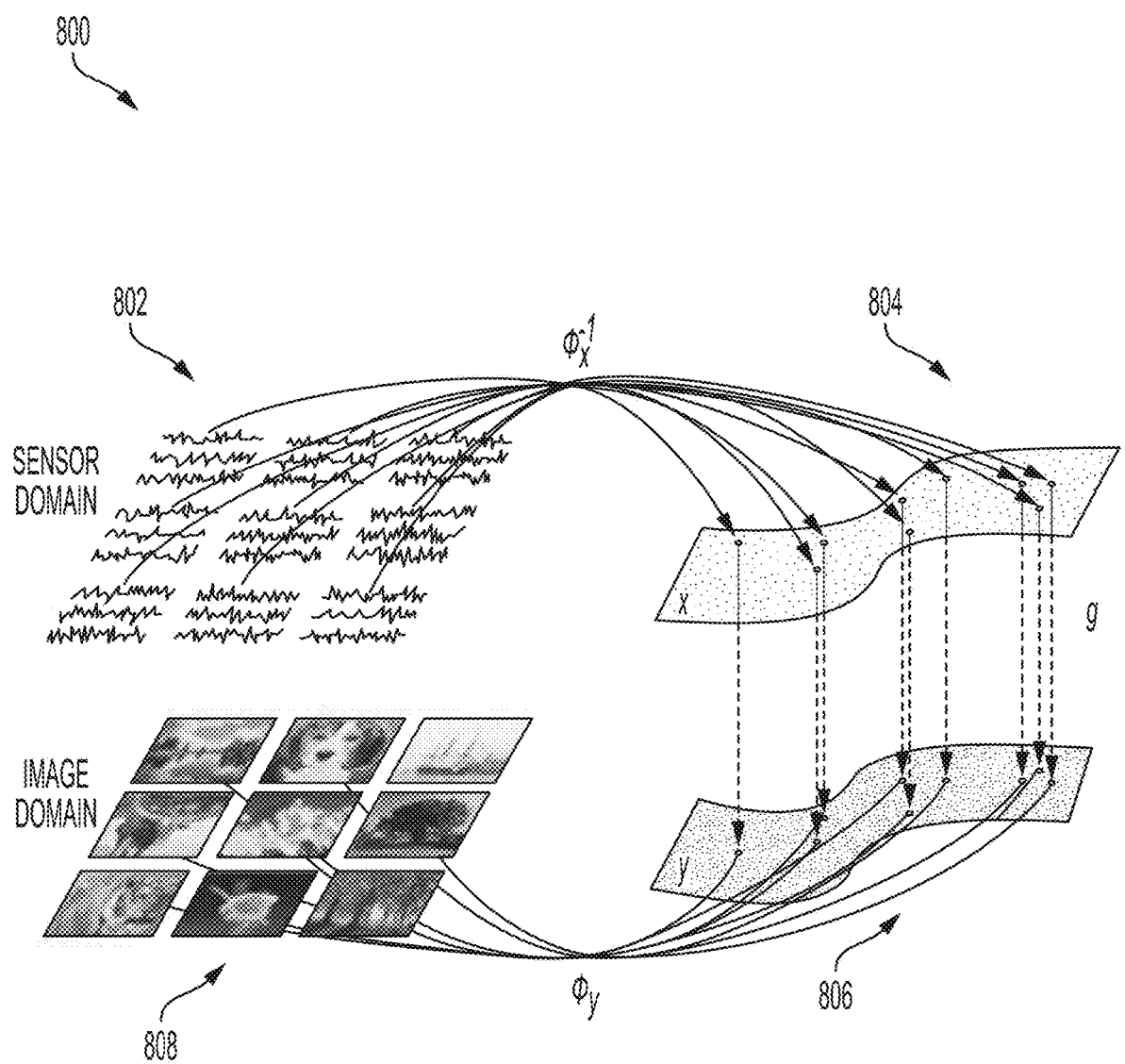
FIG. 8 shows a flow diagram illustrating an example process for image reconstruction between a sensor domain and an image domain using a data-driven, manifold learning approach, in accordance with some aspects of the disclosure.

FIG. 8 shows a flow diagram illustrating an example process 800 for image reconstruction between a sensor domain and an image domain using a data-driven, manifold learning approach (e.g., using neural networks). Sensor data 802 may be generated when an image is captured using any one of a variety of imaging systems including, but not limited to, a magnetic resonance imaging (Mill) system, a computed tomography (CT) scanning system, a positron emission tomography (PET) scanning system, an ultrasound system, an optical complementary metal oxide semiconductor (CMOS) imaging system, and an optical charge coupled device (CCD) image sensor. Sensor data 802 may be acquired or encoded in a particular domain corresponding to the particular method of image capture used to acquire/generate the sensor data 802, which can be referred to herein as the "sensor domain". Any noise that may be present within the sensor data 802 (e.g., as a result of non-idealities involved with image capture) is inherently intertwined with the sensor data. As noted, the sensor data 802 may be encoded in one of a variety of different domains (e.g., frequency domain, Radon domain, etc.) depending on the method of data acquisition used, the domain of any given set of sensor data may be referred to herein generally as the sensor domain. By transforming the sensor data 802 from the sensor domain to the image domain to produce image data 808, the sensor data 802 may be effectively decoded.

In FIG. 8, x represents the sensor data 802 in the sensor domain, and y represents image data 808 in the image domain. Given $\tilde{x}$, the noisy observation of sensor domain data x, the stochastic projection operator onto X: $p(\tilde{x})=P(x|\tilde{x})$ may be learned. After obtaining X, the second task is to reconstruct $f(x)$ by producing a reconstruction mapping $\hat{f}: \mathbb{R}^{n^2} \to \mathbb{R}^{n^2}$ that minimizes the reconstruction error $L(\hat{f}(x), f(x))$.

With this starting context, the reconstruction process can be described for an idealized scenario, for example, where the input sensor data are noiseless. Denote the data as $(y_i, x_i)_{i=1}^n$, where for $i^{th}$ observation $x_i$ indicates a n×n set of input parameters, and $y_i$ indicates the n×n real, underlying images. It may be assumed:

1) That there exists an unknown smooth and homeomorphic function $f: \mathbb{R}^{n^2} \to \mathbb{R}^{n^2}$, such that $y=f(x)$, and
2) That $(x_i)_{i=1}^n, (y_i)_{n=1}^n$ lie on unknown smooth manifolds $\chi$ and $y$ (e.g., manifolds 804 and 806), respectively.

Both manifolds 804 and 806 are embedded in the ambient space $\mathbb{R}^{n^2}$, such that dim $(\chi) < n^2$ and dim $(\mathcal{Y}) < n^2$. The above two assumptions combine to define a joint manifold $\mathcal{M}_{\chi,y} = \chi \times \mathcal{Y}$ that the dataset $(x_i, y_i)_{i=1}^n$ lies in, which can be written as:

$$\mathcal{M}_{\chi,y} = \{(x, f(x)) \in \mathbb{R}^{n^2} \times \mathbb{R}^{n^2} | x \in \chi, f(x) \in \mathcal{Y}\}$$

Note that (x, $f(x)$) is described using the regular Euclidean coordinate system. However, we may equivalently describe this point using the intrinsic coordinate system of $\mathcal{M}_{\chi,y}$ as (z, g(z)) such that there exists a homeomorphic mapping $\phi=(\phi_x, \phi_y)$ between (x, $f(x)$) and (z, g(z)). (i.e., $x=\phi_x(z)$ and $f(x)=\phi_y \circ g(z)$). As a side note, in topology, $\phi=(\phi_x, \phi_y)$: $\mathcal{M}_{\chi,y} \propto \mathbb{R}^{n^2} \times \mathbb{R}^{n^2}$ may correspond to the local coordinate chart of $\mathcal{M}_{\chi,y}$ at the neighborhood of (x, $f(x)$). Instead of directly learning $f$ in the ambient space, it may be desirable to learn the diffeomorphism g between $\chi$ and $\mathcal{Y}$ in order to take advantage of the low-dimensional nature of embedded space. Consequently, the process of generating $y=f(x)$ from x can be written as a sequence of function evaluations:

$$f(x) = \phi_y \circ g \circ \phi_x^{-1}(x)$$

For the convenience of later presentation, notice that given input image x, the output image follows a probability distribution $Q(Y|X=x, f)$, which is a degenerate distribution with point mass at $y=f(x)$.

With the context provided by this idealized sensor data that is free of noise in place, a non-ideal scenario, where noise or other corruption exists in the sensor domain input and a corresponding de-noising process, are now described. Instead of observing the perfect input data $x_i$, $\tilde{x}_i$ is observed, which is sensor data with noise or a corrupted version of $x_i$ by some known noise or corruption process described by the probability distribution $P(\tilde{X}|X=x)$. In order to handle this complication, a denoising step $Q(X|\tilde{X}=\tilde{x}, p)$ may be used to our model pipeline, such that our prediction for y is no longer a deterministic value, but a random variable with conditional distribution $P(Y|\tilde{X})$ so that the prediction uncertainty caused by the corruption process may be properly characterized.

Instead of learning this denoising step explicitly, an analogy may be drawn from denoising autoencoders. The joint distribution $P(Y, X, \tilde{X})$ may be modeled instead. Specifically, in addition to the assumptions (1)-(2) listed above, also assume:

3) That the true distribution $P(X|\tilde{X})$ lies in the semiparametric family $\mathbb{Q}$ defined by its first moment $\mathbb{Q}=\{Q(X|\tilde{X}=\tilde{x}, p)|E(X)=p(\tilde{X})\}$.

$P(Y, X, \tilde{X})$ may be modeled using the decomposition below:

$$Q_{(f,p)}(Y,X,\tilde{X})=Q(Y|X,f)Q(X|\tilde{X},p)P(\tilde{X})$$

In this decomposition, $Q(Y|X, f)$ denotes the model for reconstruction process described above, $Q(X|\tilde{X}, p)$ denotes the de-noising operator, and $P(\tilde{X})$ denotes the empirical distribution of corrupted images. Notice that the models for de-noising and reconstruction processes may be combined together by collapsing the first two terms on the right-hand side into one term, which gives:

$$Q_{(f,p)}(Y,X,\tilde{X})=Q(Y,X|\tilde{X},(f,p))P(\tilde{X})$$

It should be noted that $Y=f(X)$ is a deterministic and homeomorphic mapping of X; therefore, $Q(Y, X|\tilde{X}, (f,p))=Q(Y|\tilde{X}, (f, p))$ is the predictive distribution of output image y given the noisy input $\tilde{x}$, which is the estimator of interest. Consequently, the model can be written as:

$$Q_{(f,p)}(Y,X,\tilde{X})=Q(Y|\tilde{X},(f,p))P(\tilde{X})$$

This then represents a definition of the model for the joint distribution. In the actual training stage, "perfect" (e.g., substantially noiseless) input images x are available, and the model can be trained with $\tilde{x}$ that is generated from $P(\tilde{X}|X=x)$. That is to say, the joint distribution of $(Y, X, \tilde{X})$ observed in training data admits the form:

$$P(Y,X,\tilde{X})=P(Y|X)P(\tilde{X}|X)P(X)$$

The training can proceed by minimizing the KL-divergence between observed probability $P(Y, X, \tilde{X})$ and the model $Q(Y, X, \tilde{X})$, $$\mathbb{D}_{KL}\{P(Y,X,\tilde{X})\|Q_{(f,p)}(Y,X,\tilde{X})\}$$

with respect to the function-valued parameters $(f, p)$. As the KL-divergence converges toward 0, $Q(X|\tilde{X},p)$ converges to $P(X|\tilde{X})$, the de-noising projection, and at the same time $Q(Y|\tilde{X}, (f,p))$ converges to $P(Y|\tilde{X})$.

It should be noted that techniques for the explicit learning of the stochastic projection p, diffeomorphism g, and the local coordinate chart ϕ exist. However, we notice that, since $(\phi_f, \phi_x, p, g) \in \mathbb{C}^\infty$ (where $\mathbb{C}^\infty$ denotes the set of infinitely differentiable functions), $\hat{f}=\phi_f^\circ g^\circ \phi_x^{-1}{}^\circ p$ as a whole is a continuously differentiable function on a compact subset of $\mathbb{R}^{n^2}$, and can therefore be approximated with theoretical guarantee by the universal approximation theorem.

Figure 9:
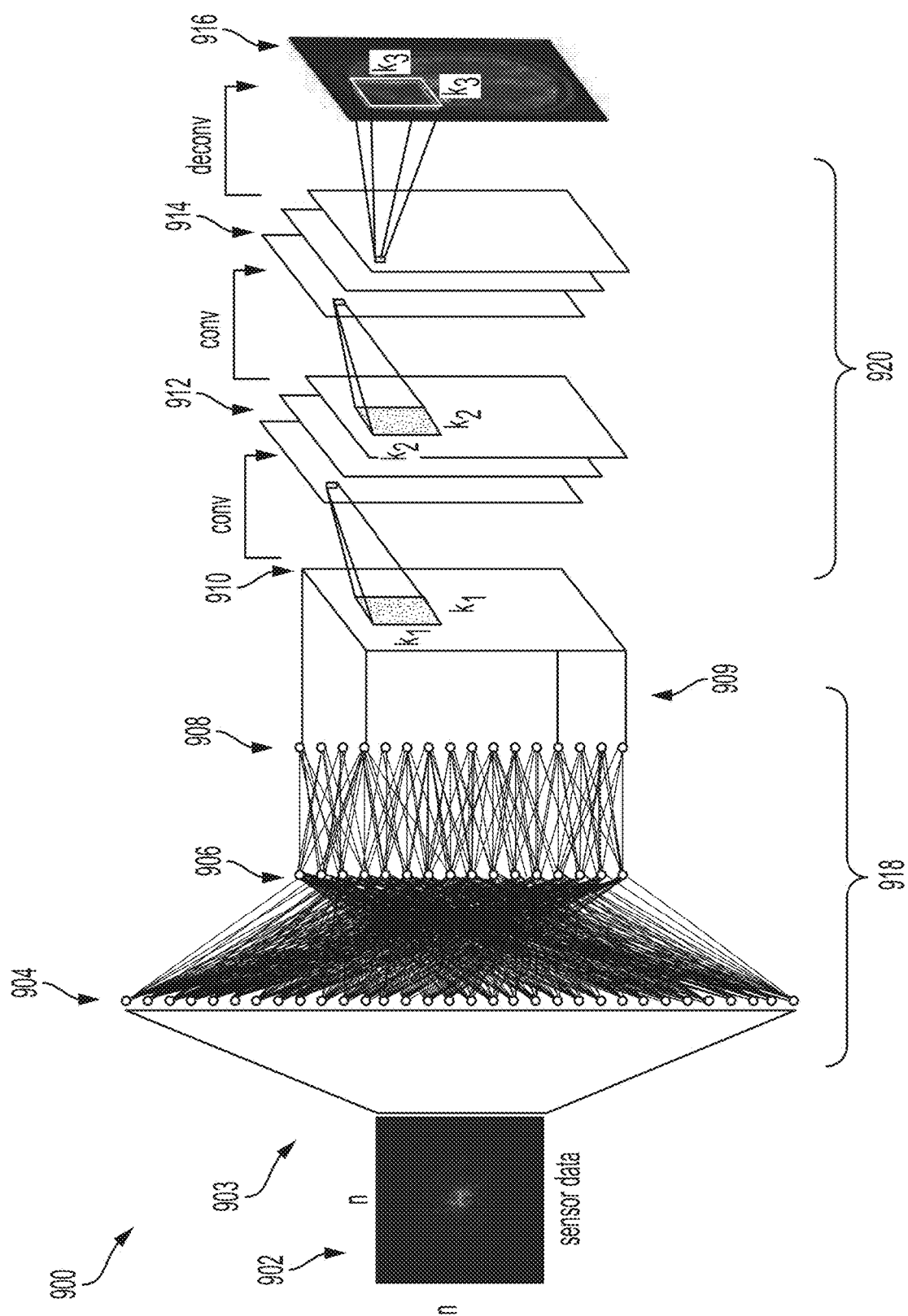
FIG. 9 shows a system diagram representing an example neural network model that can be used to reconstruct an image by transforming data from a sensor domain to an image domain, in accordance with some aspects of the disclosure.

FIG. 9 shows a system diagram representing an example neural network model 900 that can be used to reconstruct an image by transforming data from a sensor domain to an image domain. The model 900 can implement AUTOMAP image processing and, thereby, can be configured to transform sensor data (e.g., sensor data 802 of FIG. 8) from the sensor domain into the image domain, thereby reconstructing the sensor data into an image. The model 900 provides an example implementation of a data-driven, manifold learning approach as described above in connection with FIG. 8.

The sensor data 902 may be arranged in an "n×n" matrix in the sensor domain 903. The model 900 is shown to include a plurality of fully connected layers 918, including an input layer 904, a hidden layer 906, and a hidden layer 908. The fully connected layers 918 can approximate the between-manifold projection of sensor data 902 from the sensor domain 903 to the image domain 909. In this way, the fully connected layers 918 produce an "n×n" matrix 910. The matrix 910 can then processed by a plurality of convolutional layers 920, as shown, which can include both a first convolutional layer 912 and second convolutional layer 914, used to produce a reconstructed image at an output layer 916. Here, "n" represents the number of data points along a single dimension of the sensor data 902.

The sensor data 902 may include a vector or matrix of sensor domain sampled data produced, for example, by an imaging system (e.g., one of the imaging systems of FIGS. 1-7). The input layer 904 may be fully connected to the first hidden layer 906, which may allow the sensor data 902 to be vectorized in any order. Complex data in the sensor data 902 (e.g., such as MR data) may be separated into real and imaginary components and concatenated in an input vector at input layer 904. As a result, the "n×n" matrix of the sensor data 902 may be reshaped to a "$2n^2 \times 1$" real-valued vector (e.g., the input vector) containing both the real and imaginary components of the sensor data 902. The input layer 904 may be fully connected to the "$n^2 \times 1$" first hidden layer 906 that is activated by an activation function (e.g., a non-linear activation function such as the hyperbolic tangent function). The first hidden layer 906 may be fully connected to a second "$n^2 \times 1$" hidden layer 908, which may produce a "n×n" matrix 910 when applied to the output of the first hidden layer 906. Each of the fully connected layers 918 may represent affine mapping (e.g., matrix multiplication) followed by non-linearity (e.g., an activation function). For example, the non-linearity applied during the application of the first hidden layer 906 to the input vector (e.g., to the nodes of the input vector) may be represented by the following equation:

$$g(\chi)=s(W\chi+b)$$

In the above equation, g(x) is a matrix (e.g., the nodes/output of the first hidden layer) resulting from the application of the first hidden layer 906 to the input vector, where x is the input vector (e.g., the nodes/output of the input layer), where W is a d'×d weight matrix, where b is an offset vector of dimensionality d', and where s is the activation function (e.g., the hyperbolic activation function). The non-linearity applied during the application of the second hidden layer 908 to the output of the first hidden layer 906 (e.g., to the nodes of the first hidden layer) may be similarly represented.

The first convolutional layer 912 may apply a predetermined number of filters to the matrix 910 followed by a rectifier nonlinearity. The second convolutional layer 914 may apply a predetermined number of filters to the output of the first convolutional layer 912 followed by a rectifier nonlinearity. The output of the second convolutional layer 914 may be de-convolved with a predetermined number of filters by applying the output layer 916 to produce a reconstructed image in the image domain (e.g., as an "n×n" matrix). In this way, the first and second convolutional layers 912, 914 may be applied to perform feature extraction after the sensor data 902 is transformed from the sensor domain 903 into the image domain 909.

The model 900 can be trained to perform image reconstruction before being implemented. For example, an image may be transformed from the image domain 909 to a given sensor domain 903 (e.g., frequency domain, Radon domain, etc.) using known operations to produce sensor data 902. This sensor data 902 may then be input into and processed by model 900 to perform training. The output of model 900 may then be analyzed and compared to the original image to determine the amount of error present in the reconstructed image. The weights of the networks within the model 900 (e.g., the weights between layers 904 and 906 and between layers 906 and 908) may then be adjusted, and then this training process may be repeated with a new training image. For example, the training process may be repeated a predetermined number of times or may be repeated until the amount of observed error in the reconstructed image is observed to be below a certain threshold.

For instances in which the model 900 is intended to be used for a particular image reconstruction purpose (e.g., reconstructing images of the human brain), it may be beneficial to train the model 900 using images related to that purpose (e.g., using images of the human brain). This image-based training specialization may result in improved hidden-layer activation sparsity for fully connected layers 918 of the model 900 without the need to impose a sparsifying penalty on these layers. Improving hidden layer activation sparsity in this way may provide benefits over comparatively dense hidden layer activations. For example, these benefits may include reduced information entangling, more efficient variable-size representation, improved likelihood of linear separability, and improved efficiency, compared to dense hidden layer activations.

Figure 10:
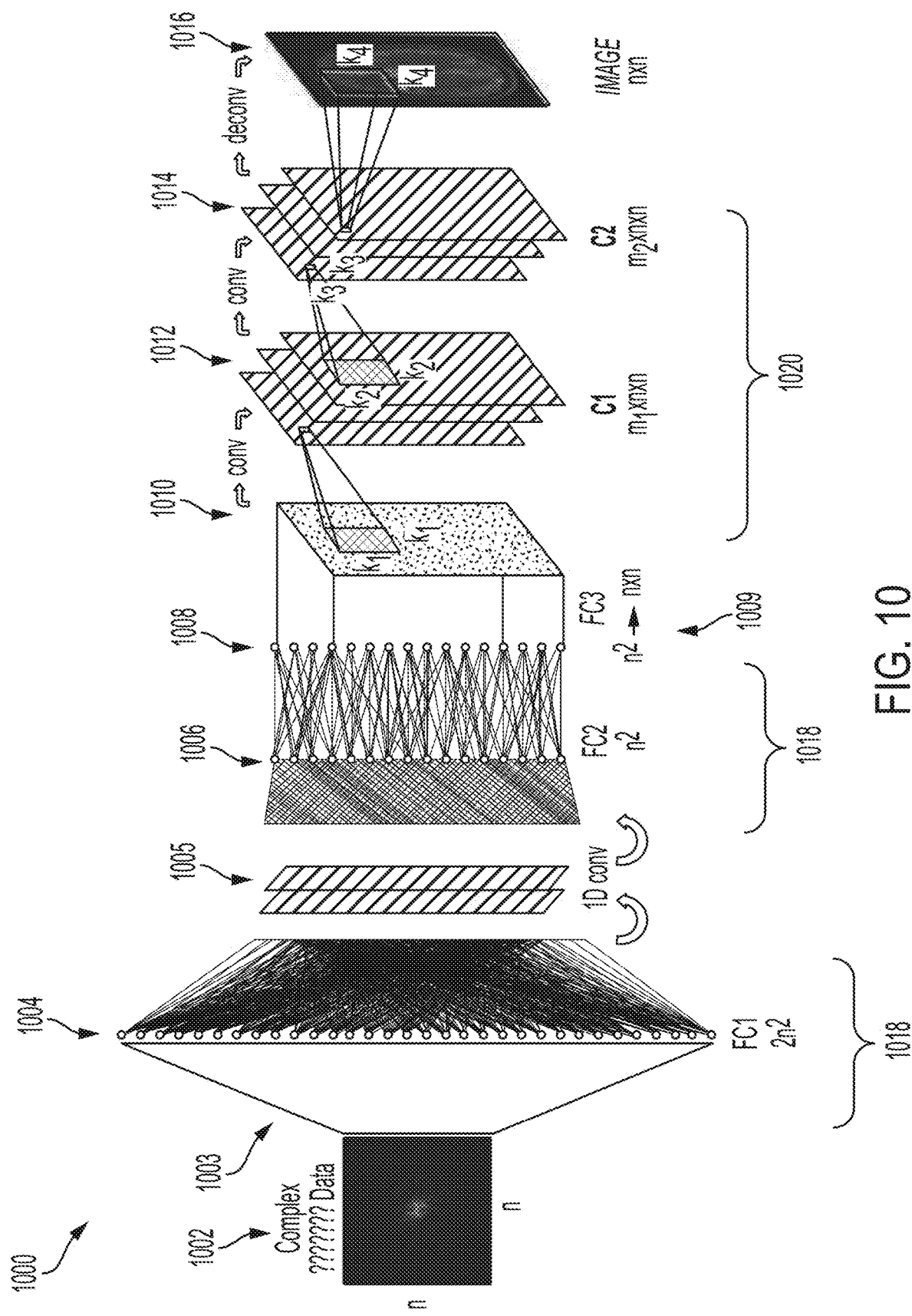
FIG. 10 shows a system diagram representing another example neural network model that can be used to reconstruct an image by transforming data from a sensor domain to an image domain, in accordance with some aspects of the disclosure.

FIG. 10 shows a system diagram representing another example neural network model 1000 that can be used to reconstruct an image by transforming data from a sensor domain to an image domain. The model 1000 can implement AUTOMAP image processing and, thereby, can be configured to transform sensor data (e.g., sensor data 802 of FIG. 8) from the sensor domain into the image domain, thereby reconstructing the sensor data into an image. The model 1000 provides another example implementation of a data-driven, manifold learning approach as described above in connection with FIG. 8.

The model 1000 is shown to receive as input raw sensor data 1002 that may be arranged in an "n×n" matrix in the sensor domain 1003. The model 1000 is also shown to include a plurality of fully connected layers 1018, including an input layer 1004, a first hidden layer 1006, and a second hidden layer 1008. The model 1000 is further shown to include a first convolutional layer 1005 placed between the input layer 1004 and the first hidden layer 1006. The fully connected layers 1018 can approximate the between-manifold projection of sensor data 1002 from the sensor domain 1003 to the image domain 1009. In this way, the fully connected layers 1018 produce an "n×n" matrix 1010. The matrix 1010 can then processed by a plurality of convolutional layers 1020, as shown, which can include both a second convolutional layer 1012 and a third convolutional layer 1014, used to produce a reconstructed image at an output layer 1016. Here, "n" represents the number of data points along a single dimension of the sensor data 1002.

The sensor data 1002 may include a vector or matrix of sensor domain sampled data produced, for example, by an imaging system (e.g., one of the imaging systems of FIGS. 1-7). The sensor data 1002 can be applied to the input layer 1004 such that model 1000 reorganizes the input data 1002 used for AUTOMAP image reconstruction such that the real and imaginary components of each sample of the input data 1002 are placed adjacent to each other as opposed to being separated and concatenated along a single input dimension as in the model 900. The specific organization of the real and imaginary components of the input data 1002 in this manner using the model 1000 can provide improvements in terms of model accuracy and thereby can provide improvements in image reconstruction when compared to the model 900.

Figure 11:
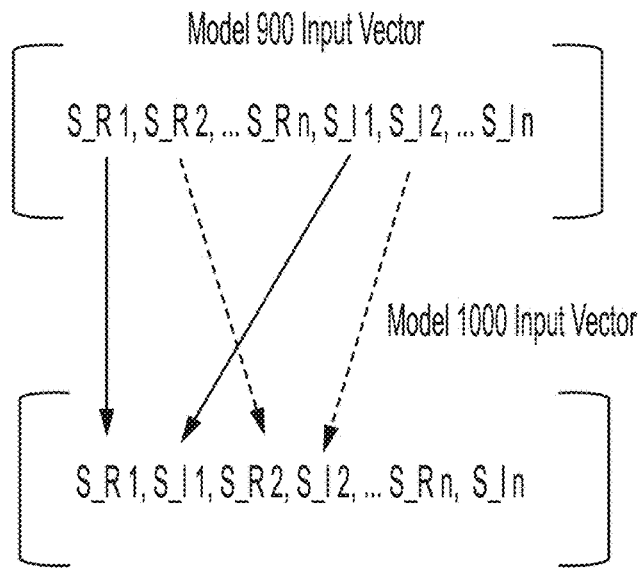
FIG. 11 shows an example input vector that can be used by the neural network model of FIG. 9 as well as an example input vector that can be used by the neural network model of FIG. 10, in accordance with some aspects of the disclosure.
Figure 12:
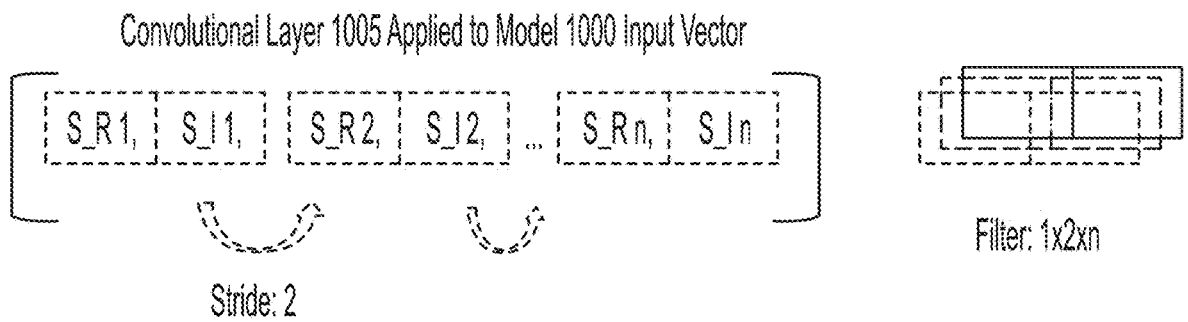
FIG. 12 shows an example of a convolutional layer of the neural network model of FIG. 10 being applied to an input vector, in accordance with some aspects of the disclosure.

FIG. 11 shows an example input vector 930 that can be used by model 900 as well as an example input vector 1030 that can be used by model 1000. As shown, in input vector 930, the real and imaginary components of the input data 902 are separated and concatenated along a single input dimension. In contrast, in the input vector 1030, the real and imaginary components of each sample of the input data 1002 are placed adjacent to each other. FIG. 12 shows an example of the first convolutional layer 1005 being applied to input vector 1030. As shown, the first convolutional layer 1005 has a kernel of 2 and a stride of 2 such that the first convolutional layer 1005 can take the neighboring real and imaginary components of each sample in the input data 1002 into account. With this design, the first convolutional layer 1005 can learn the relationship between real and imaginary components of each sample of the input data 1002, which can lead to better training results and better accuracy for the model 1000 when compared to other approaches such as the model 900.

Accordingly, input layer 1004 can transform the "n×n" matrix of the sensor data 1002 to a "$2n^2 \times 1$" real-valued vector (e.g., the input vector 1030) containing both the real and imaginary components of the sensor data 1002 such that the real and imaginary components of each sample of the input data 1002 are placed adjacent to each other. The input vector 1030 can then be applied to the first convolutional layer 1005 to generate a filtered input vector 1040. As such, the first convolutional layer 1005 can be one-dimensional convolutional layer. The first convolutional layer 1005 can apply a predetermined number of filters to input vector 1030 followed by a rectifier nonlinearity to generate the filtered input vector 1040.

The filtered input vector 1040 can then be applied to the "$n^2 \times 1$" first hidden layer 1006 that is activated by an activation function (e.g., a non-linear activation function such as the hyperbolic tangent function). The first hidden layer 1006 may be fully connected to a second "$n^2 \times 1$" hidden layer 1008, which may then produce a "n×n" matrix 1010 when applied to the output of the first hidden layer 1006. Each of the fully connected layers 1018 may represent affine mapping (e.g., matrix multiplication) followed by non-linearity (e.g., an activation function), such as detailed above with respect to model 900.

The second convolutional layer 1012 may apply a predetermined number of filters to the matrix 1010 followed by a rectifier nonlinearity. The third convolutional layer 1014 may apply a predetermined number of filters to the output of the second convolutional layer 1012 followed by a rectifier nonlinearity. The output of the third convolutional layer 1014 may be de-convolved with a predetermined number of filters by applying the output layer 1016 to produce a reconstructed image in the image domain (e.g., as an "n×n" matrix). In this way, the second convolutional layer 1012 and the third convolutional layer 1014 may be applied to perform feature extraction after the sensor data 1002 is transformed from the sensor domain 1003 into the image domain 1009.

The model 1000 can be trained to perform image reconstruction before being implemented. For example, an image may be transformed from the image domain 1009 to a given sensor domain 1003 (e.g., frequency domain, Radon domain, etc.) using known operations to produce sensor data 1002. This sensor data 1002 may then be input into and processed by model 1000 to perform training. The output of model 1000 may then be analyzed and compared to the original image to determine the amount of error present in the reconstructed image. The weights of the networks within the model 1000 (e.g., the weights between layers 1004 and 1006 and between layers 1006 and 1008) may then be adjusted, and then this training process may be repeated with a new training image. For example, the training process may be repeated a predetermined number of times or may be repeated until the amount of observed error in the reconstructed image is observed to be below a certain threshold.

For instances in which the model 1000 is intended to be used for a particular image reconstruction purpose (e.g., reconstructing images of the human brain), it may be beneficial to train the model 1000 using images related to that purpose (e.g., using images of the human brain). This image-based training specialization may result in improved hidden-layer activation sparsity for fully connected layers 1018 of the model 1000 without the need to impose a sparsifying penalty on these layers. Improving hidden layer activation sparsity in this way may provide benefits over comparatively dense hidden layer activations. For example, these benefits may include reduced information entangling, more efficient variable-size representation, improved likelihood of linear separability, and improved efficiency, compared to dense hidden layer activations.

Figure 13:
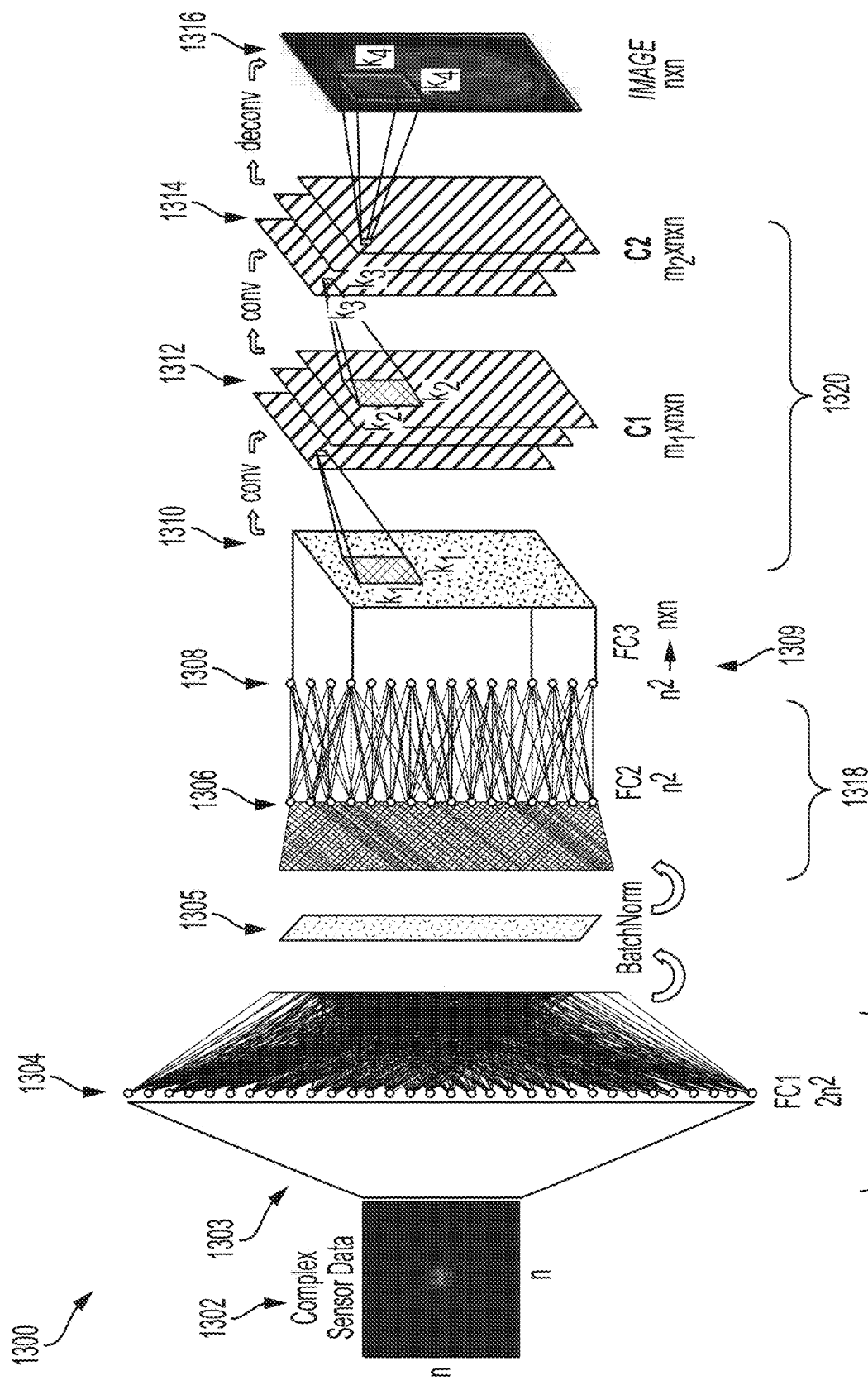
FIG. 13 shows a system diagram representing yet another example neural network model that can be used to reconstruct an image by transforming data from a sensor domain to an image domain, in accordance with some aspects of the disclosure.

FIG. 13 shows a system diagram representing yet another example neural network model 1300 that can be used to reconstruct an image by transforming data from a sensor domain to an image domain. The model 1300 can implement AUTOMAP image processing and, thereby, can be configured to transform sensor data (e.g., sensor data 802 of FIG. 8) from the sensor domain into the image domain, thereby reconstructing the sensor data into an image. The model 1300 provides yet another example implementation of a data-driven, manifold learning approach as described above in connection with FIG. 8.

The model 1300 is shown to receive as input raw sensor data 1302 that may be arranged in an "n×n" matrix in the sensor domain 1303. The model 1300 is also shown to include a plurality of fully connected layers 1318, including an input layer 1304, a first hidden layer 1306, and a second hidden layer 1308. The model 1300 is further shown to include a batch normalization layer 1305 placed between the input layer 1304 and the first hidden layer 1306. The fully connected layers 1318 can approximate the between-manifold projection of sensor data 1302 from the sensor domain 1303 to the image domain 1309. In this way, the fully connected layers 1318 produce an "n×n" matrix 1310. The matrix 1310 can then processed by a plurality of convolutional layers 1320, as shown, which can include both a first convolutional layer 1312 and a second convolutional layer 1314, used to produce a reconstructed image at an output layer 1316. Here, "n" represents the number of data points along a single dimension of the sensor data 1302.

The sensor data 1302 may include a vector or matrix of sensor domain sampled data produced, for example, by an imaging system (e.g., one of the imaging systems of FIGS. 1-7). Complex data in the sensor data 1302 can be applied to the input layer 1304 such that the "n×n" matrix of the sensor data 1302 may be reshaped to a "$2n^2 \times 1$" real-valued vector (e.g., the input vector) containing both the real and imaginary components of the sensor data 1302. In the input vector generated by input layer 1304, the real and imaginary components of the input data 1302 can be separated and concatenated along a single input dimension (e.g., similar to input vector 930), the real and imaginary components of each sample of the input data 1302 can be placed adjacent to each other (e.g., similar to the input vector 1030), or the input data 1302 can be vectorized in another suitable order.

Then, the input vector generated by the input layer 1304 and be applied to the batch normalization layer 1305 to generate a normalized input vector. The batch normalization layer 1305 can be used to make the training of model 1300 faster and more stable. For example, batch normalization layer 1305 normalize the samples contained in the input data 1302 such that the samples are re-centered, re-scaled, or any other suitable approach to normalization the distribution of samples contained in the normalized input vector. The specific arrangement of the batch normalization layer 1305 within the model 1300 can provide improved accuracy of the model 1300 when compared to some other approaches used in medical imaging application, such as model 900, as described in more detail below.

The normalized input vector can then be applied to the "$n^2 \times 1$" first hidden layer 1306 that is activated by an activation function (e.g., a non-linear activation function such as the hyperbolic tangent function). The first hidden layer 1306 may be fully connected to the second "$n^2 \times 1$" hidden layer 1308, which may produce a "n×n" matrix 1310 when applied to the output of the first hidden layer 1306. Each of the fully connected layers 1318 may represent affine mapping (e.g., matrix multiplication) followed by non-linearity (e.g., an activation function), such as detailed above with respect to model 900.

The first convolutional layer 1312 may apply a predetermined number of filters to the matrix 1310 followed by a rectifier nonlinearity. The second convolutional layer 1314 may apply a predetermined number of filters to the output of the first convolutional layer 1312 followed by a rectifier nonlinearity. The output of the second convolutional layer 1314 may be de-convolved with a predetermined number of filters by applying the output layer 1316 to produce a reconstructed image in the image domain (e.g., as an "n×n" matrix). In this way, the first and second convolutional layers 1312, 1314 may be applied to perform feature extraction after the sensor data 1302 is transformed from the sensor domain 1303 into the image domain 1309.

The model 1300 can be trained to perform image reconstruction before being implemented. For example, an image may be transformed from the image domain 1309 to a given sensor domain 1303 (e.g., frequency domain, Radon domain, etc.) using known operations to produce sensor data 1302. This sensor data 1302 may then be input into and processed by model 1300 to perform training. The output of model 1300 may then be analyzed and compared to the original image to determine the amount of error present in the reconstructed image. The weights of the networks within the model 1300 (e.g., the weights between layers 1304 and 1306 and between layers 1306 and 1308) may then be adjusted, and then this training process may be repeated with a new training image. For example, the training process may be repeated a predetermined number of times or may be repeated until the amount of observed error in the reconstructed image is observed to be below a certain threshold.

For instances in which the model 1300 is intended to be used for a particular image reconstruction purpose (e.g., reconstructing images of the human brain), it may be beneficial to train the model 1300 using images related to that purpose (e.g., using images of the human brain). This image-based training specialization may result in improved hidden-layer activation sparsity for fully connected layers 1318 of the model 1300 without the need to impose a sparsifying penalty on these layers. Improving hidden layer activation sparsity in this way may provide benefits over comparatively dense hidden layer activations. For example, these benefits may include reduced information entangling, more efficient variable-size representation, improved likelihood of linear separability, and improved efficiency, compared to dense hidden layer activations.

Figure 14A:
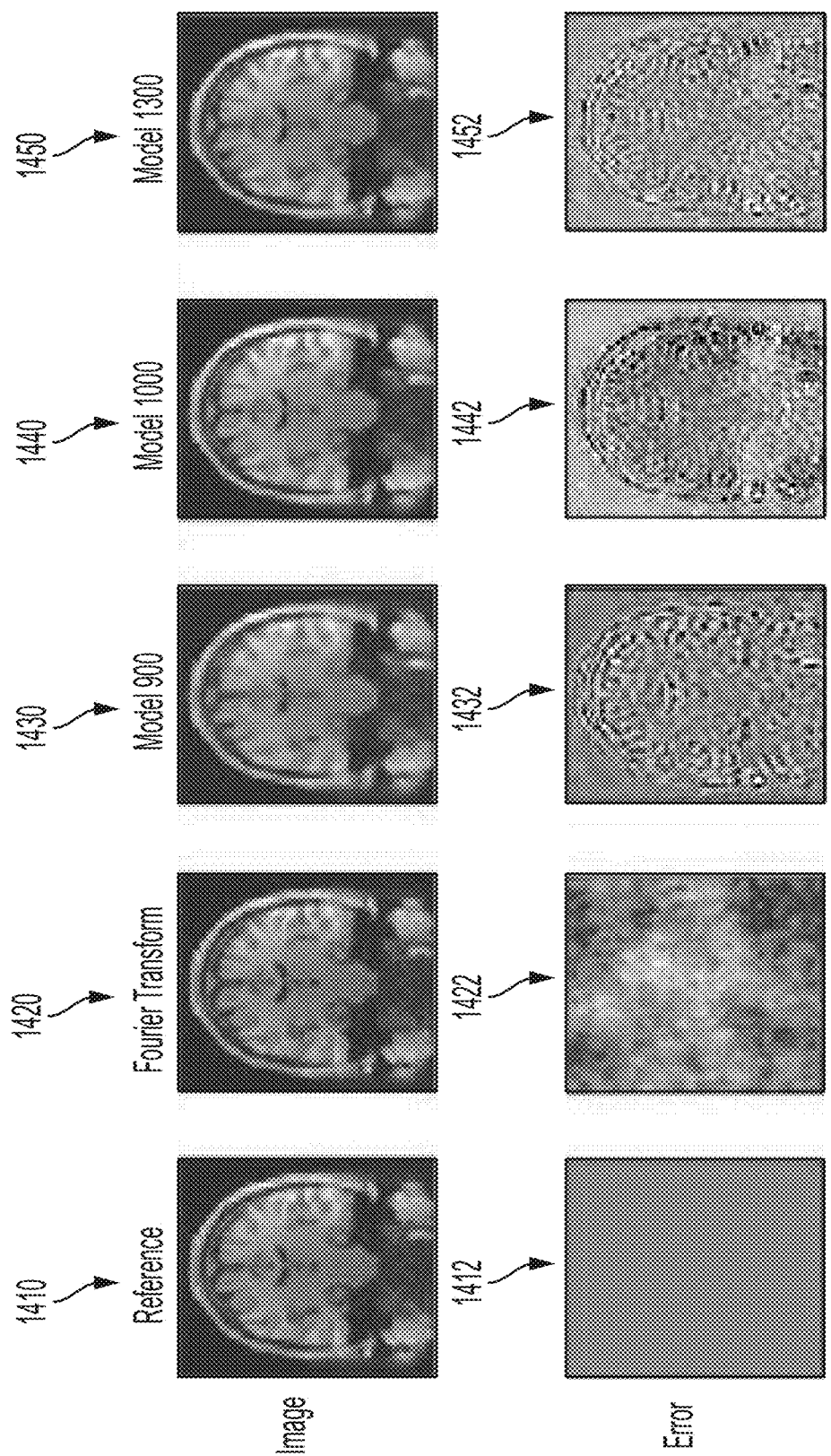
FIG. 14A shows a first series of example medical images that are generated using different approaches and their associated errors, in accordance with some aspects of the disclosure.

FIG. 14A shows a first series of example medical images that are generated using different approaches and their associated errors. Image 1410 shows a reference medical image of a human brain (a brain MM). The error 1412 for the reference image 1410 is zero. Image 1420 shows the result of using a more conventional Fourier transform reconstruction process (as discussed above) to reconstruct the reference image 1410. As shown, the error associated with the Fourier transform reconstruction process is significant. Image 1430 shows the result of using model 900 (as discussed above) to reconstruct the reference image 1410. As shown, the error 1432 associated with the use of model 900 is significantly reduced when compared to the Fourier transform reconstruction process. Image 1440 shows the result of using model 1000 (as discussed above, including the added first convolutional layer 1005 and the specific ordering of the complex input data such that real and imaginary components of each sample of the input data 1002 are placed adjacent to each other) to reconstruct the reference image 1410. As shown, the error 1442 is also significantly reduced when compared to the Fourier transform reconstruction process. Image 1450 shows the result of using model 1300 (as discussed above, including the added batch normalization layer 1305) to reconstruct the reference image 1410. As shown, the error 1452 is again significantly reduced when compared to the Fourier transform reconstruction process.

Figure 14B:
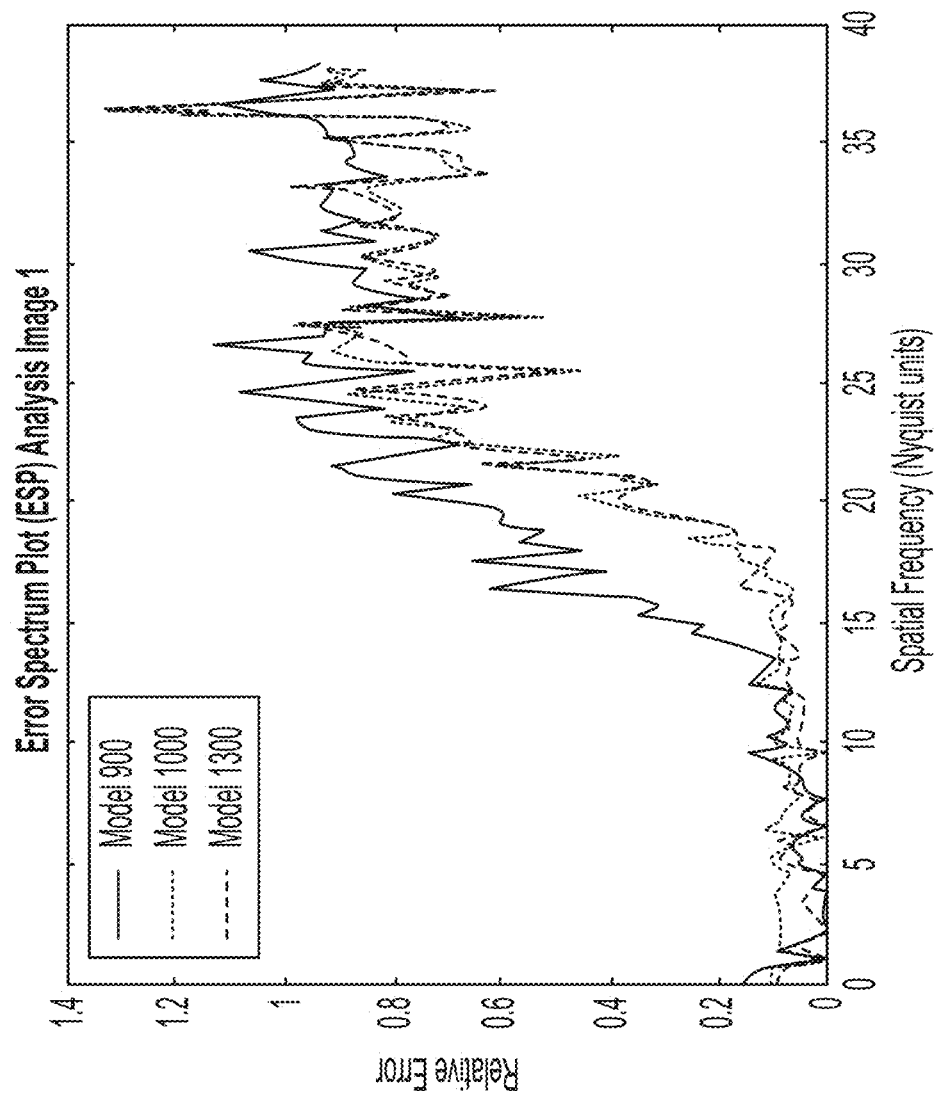
FIG. 14B shows a graph plotting the relative error of the different imaging approaches of FIG. 14A as a function of spatial frequency, in accordance with some aspects of the disclosure.

FIG. 14B shows a graph plotting the relative error of the different imaging approaches shown in FIG. 14A as a function of spatial frequency. The data shown in the graph of FIG. 14B was generated using a Fourier Radial Error Spectrum Plot (ESP) analysis. In the graph of FIG. 14B, separate plots showing the relative error associated with the use of model 900, model 1000, and model 1300 to reconstruct the reference image 1410 as a function of spatial frequency (in Nyquist units) are shown. It can be seen from the graph of FIG. 14B that the relative error associated with the use of model 1000 and model 1300 is noticeably lower than the relative error associated with the use of model 900. This data suggests that the use of the added first convolutional layer 1005 and the specific ordering of the complex input data such that real and imaginary components of each sample of the input data 1002 are placed adjacent to each other (in model 1000) as well as the added batch normalization layer 1305 (in model 1300) can be used to improve the accuracy of model 900. In the aggregate, the specific ordering of the complex input data such that real and imaginary components of each sample of the input data 1002 are placed adjacent to each other (in model 1000) as well as the added batch normalization layer 1305 (in model 1300) can be used to improve the accuracy of model 900 by about a factor of two.

FIG. 15A shows a second series of example medical images that are generated using different approaches and their associated errors. Image 1510 shows a reference medical image of a human heart (a heart MM). The error 1512 for the reference image 1510 is zero. Image 1520 shows the result of using a Fourier transform reconstruction process to reconstruct the reference image 1510. As shown, the error associated with the Fourier transform reconstruction process is significant. Image 1530 shows the result of using model 900 to reconstruct the reference image 1510. As shown, the error 1532 associated with the use of model 900 is significantly reduced when compared to the Fourier transform reconstruction process. Image 1540 shows the result of using model 1000 to reconstruct the reference image 1510. As shown, the error 1542 is also significantly reduced when compared to the Fourier transform reconstruction process. Image 1550 shows the result of using model 1300 to reconstruct the reference image 1510. As shown, the error 1552 is again significantly reduced when compared to the Fourier transform reconstruction process.

Figure 15B:
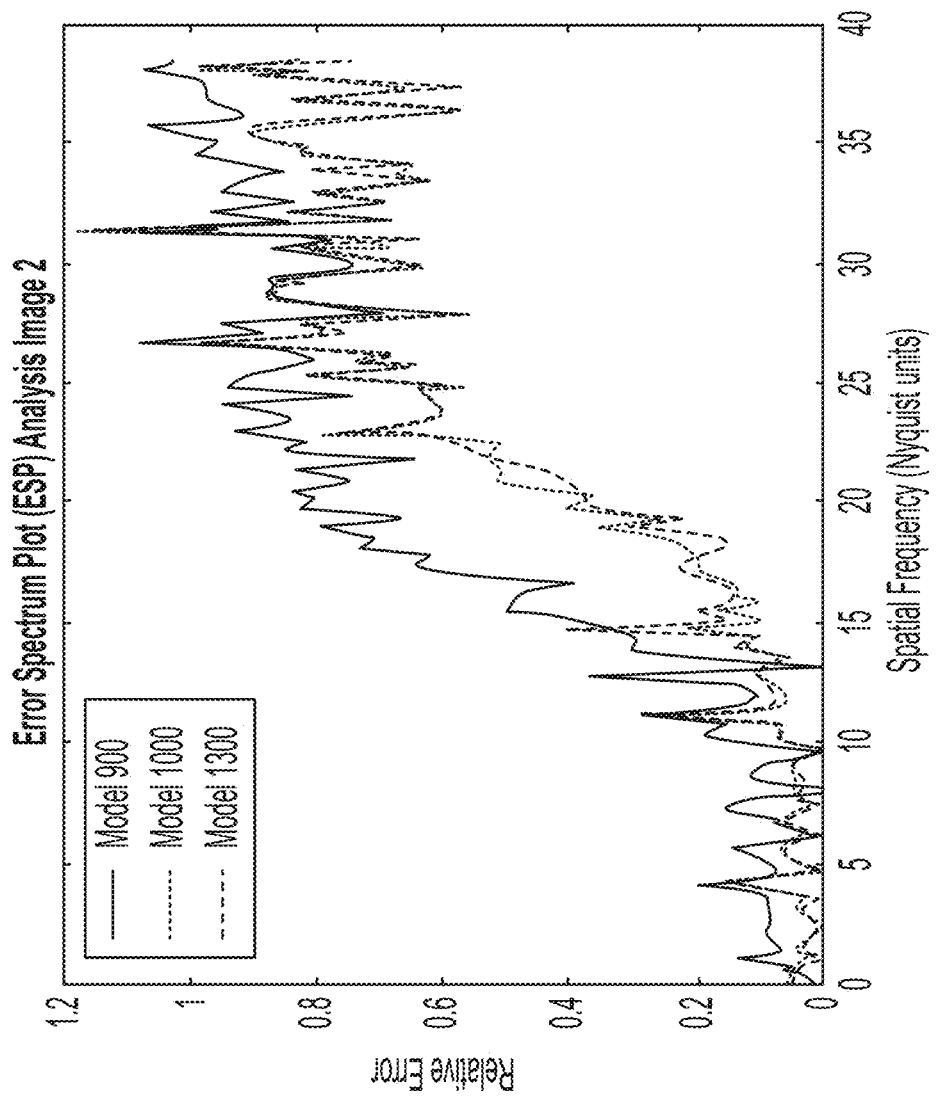
FIG. 15B shows a graph plotting the relative error of the different imaging approaches of FIG. 15A as a function of spatial frequency, in accordance with some aspects of the disclosure.

FIG. 15B shows a graph plotting the relative error of the different imaging approaches shown in FIG. 15A as a function of spatial frequency. The data shown in the graph of FIG. 15B was generated using a Fourier Radial Error Spectrum Plot (ESP) analysis. In the graph of FIG. 15B, separate plots showing the relative error associated with the use of model 900, model 1000, and model 1300 to reconstruct the reference image 1510 as a function of spatial frequency (in Nyquist units) are shown. It can be seen from the graph of FIG. 15B that the relative error associated with the use of model 1000 and model 1300 is again noticeably lower than the relative error associated with the use of model 900. This data again suggests that the use of the added first convolutional layer 1005 and the specific ordering of the complex input data such that real and imaginary components of each sample of the input data 1002 are placed adjacent to each other (in model 1000) as well as the added batch normalization layer 1305 (in model 1300) can be used to improve the accuracy of model 900. In the aggregate, the specific ordering of the complex input data such that real and imaginary components of each sample of the input data 1002 are placed adjacent to each other (in model 1000) as well as the added batch normalization layer 1305 (in model 1300) can again be used to improve the accuracy of model 900 by about a factor of two.

Figure 16:
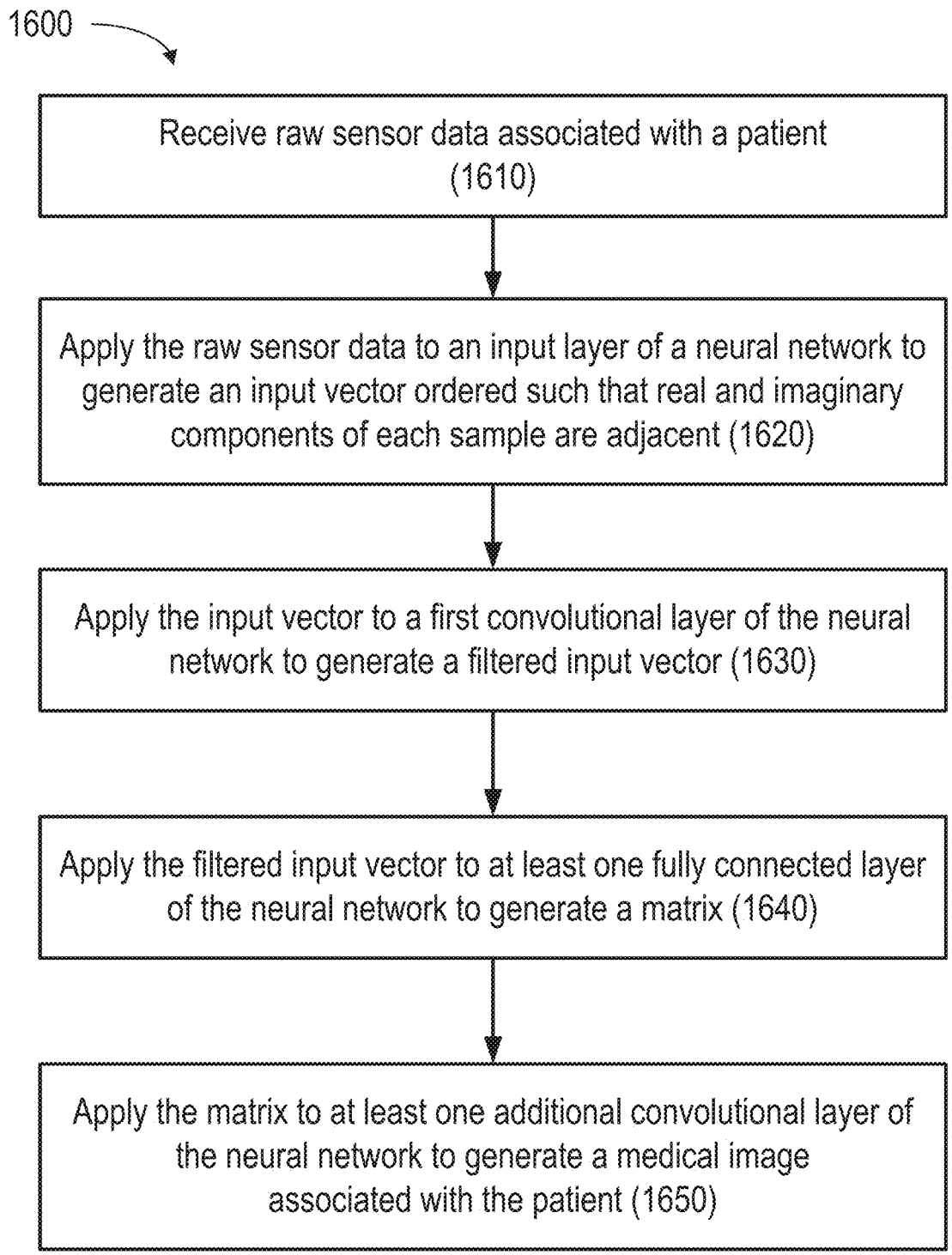
FIG. 16 shows a flow diagram illustrating an example process for medical imaging, in accordance with some aspects of the disclosure, in accordance with some aspects of the disclosure.

FIG. 16 shows a flow diagram illustrating an example process 1600 for medical imaging. Process 1600 can be performed by a variety of different systems, such as any of the imaging systems of FIGS. 1-7 as detailed above. Moreover, machine-readable instructions for performing process 1600 can be provided via a variety of different types of computer-readable media, including non-transitory computer-readable media. Process 1600 can be used to improve the accuracy of various image reconstruction processes for medical imaging applications (and potentially other imaging applications) by specifically ordering complex input data such that the real components and the imaginary components of each sample of the complex input data are placed adjacent to each other. Moreover, a filter such as a convolutional filter can then be applied to the ordered complex input data in order to learn the relationship between the real and imaginary components of the complex input data. Process 1600 can be performed using a trained model (e.g., a trained neural network) such as model 1000 described above. It will also be appreciated that process 1600 can be adapted based on model 1300 as described above.

At 1610, process receives raw sensor data associated with a patient. For example, model 1000 can receive the sensor data 1002 associated with a patient. The input data can be arranged in a matrix, arranged in a vector, etc. in the sensor domain. The input data can include sampled data generated by a variety of different imaging systems and other types of systems, such as any of the imaging systems described above with respect to FIGS. 1-7 (e.g., an x-ray CT system, an Mill system, an ultrasound system, etc.). The raw sensor data can be raw Mill k-space data as described above, for example.

At 1620, process 1600 can apply the raw sensor data to an input layer of a neural network to generate an input vector ordered such that real and imaginary components of each sample in the raw sensor data are adjacent to each other (e.g., interleaved). For example, the sensor data 1002 can be applied to the input layer 1004 to generate the input vector 1030. At 1630, process 1600 can apply the input vector to a first convolutional layer of the neural network to generate a filtered input vector. For example, the input vector 1030 output from the input layer 1004 can be applied to the first convolutional layer 1005 to generate the filtered input vector 1040. With this design, the first convolutional layer can learn the relationship between the real and imaginary components of each sample of the raw sensor data, which can lead to better training results and better accuracy of the neural network, and thereby better image reconstruction.

At 1640, process 1600 can apply the filtered input vector to at least one fully connected layer of the neural network to generate a matrix. For example, the filtered input vector 1040 can be applied to the hidden layer 1006 and/or the hidden layer 1008 to generate the matrix 1010. At 1650, process 1600 can apply the matrix to at least one additional convolutional layer of the neural network different from the first convolutional layer to generate a medical image associated with the patient. For example, the matrix 100 can be applied to the second convolutional layer 1012 and/or the third convolutional layer 1014, as well as the output layer 1016, to generate the reconstructed output image (e.g., image 1440, image 1540). The generated image can then be displayed for clinical analysis of the reconstructed output image of the patient. As shown for example in the data plotted in FIG. 14B and FIG. 15B, the specific ordering of the input vector and the application of the input vector to the first convolutional layer can provide improvements in the accuracy of the neural network used to generate the medical image associated with the patient.

FIG. 17 shows a table illustrating mean squared error (MSE) data values and root mean squared error (RMSE) data values associated with different medical image generation approaches, including using a Fourier transform, using the model 900, using the model 1000, and using the model 1300. As in the graphs of FIG. 14B and FIG. 15B, it can be seen from the data provided in the table of FIG. 17 that using the model 1000 and using the model 1300 can provide improvements in terms of accuracy when generating medical images.

Using the data-driven manifold learning techniques described above, opposed to conventional data transformation techniques such as the Discrete Fourier Transform, the domain for signal acquisition may be comparatively more flexible and can be more tailored to the underlying physical system. This generalized reconstruction can compensate for hardware imperfections such as gradient nonlinearity in Mill by being trained on the system being used. These and other imaging artifacts can be compensated for by the trained neural network. Also, generalized reconstruction may have higher noise immunity and reduced under sampling error when appropriately trained, allowing for greatly accelerated image capture. Additionally, non-intuitive Pulse sequences (e.g., for Mill applications) may be generated by data-driven manifold learning because the signals can be acquired in a non-intuitive domain before reconstruction. Further, pulse sequences can be tailored in real-time in response to specific individual subjects or samples. Training may, for example, be performed with large public or private image databases (e.g., PACS, Human Connectome Project, etc.).

It will be appreciated that this description uses examples to disclose the invention and also to enable any person skilled in the art to practice the invention, including making and using any devices or systems and performing any incorporated methods. The patentable scope of the invention is defined by the claims and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A method for medical imaging, comprising:
   receiving raw sensor data acquired from a patient using a medical imaging modality;
   applying the raw sensor data to an input layer of a neural network to generate an input vector, wherein the input layer of the neural network orders the input vector such that a real component and an imaginary component of each sample in the raw sensor data are adjacent to each other;
   applying the input vector to a first convolutional layer of the neural network to generate a filtered input vector;
   applying the filtered input vector to at least one fully connected layer of the neural network to generate a matrix;
   applying the matrix to at least one additional convolutional layer of the neural network different from the first convolutional layer to generate a medical image of the patient; and
   displaying the medical image of the patient.

2. The method of claim 1, wherein the first convolutional layer has a kernel of two and a stride of two.

3. The method of claim 2, wherein the input vector comprises a one-dimensional vector and the first convolutional layer comprises a one-dimensional convolutional layer.

4. The method of claim 1, wherein applying the filtered input vector to the at least one fully connected layer of the neural network to generate the matrix comprises:
   applying the filtered input vector to a first hidden layer activated by a first activation function; and
   applying an output of the first hidden layer to a second hidden layer activated by a second activation function to generate the matrix.

5. The method of claim 1, wherein the raw sensor data comprises raw magnetic resonance imaging (MM) k-space data.

6. The method of claim 1, wherein the neural network comprises a data-driven, manifold learning neural network.

7. The method of claim 1, wherein applying the matrix to the at least one additional convolutional layer of the neural network different from the first convolutional layer to generate the medical image of the patient comprises:
applying the matrix to a second convolutional layer to filter the matrix in accordance with a first filter;
applying an output of the second convolutional layer to a third convolutional layer to filter the output of the second convolutional layer in accordance with a second filter; and
applying an output of the third convolutional layer to an output layer to generate the medical image of the patient.

8. A non-transitory computer-readable storage medium having instructions stored thereon that, when executed by at least one processor, cause the at least one processor to implement operations comprising:
receiving raw sensor data acquired from a patient using a medical imaging system;
applying the raw sensor data to an input layer of a neural network to generate an input vector, wherein the input layer of the neural network orders the input vector such that a real component and an imaginary component of each sample in the raw sensor data are adjacent;
applying the input vector to a first convolutional layer of the neural network to generate a filtered input vector;
applying the filtered input vector to at least one fully connected layer of the neural network to generate a matrix;
applying the matrix to at least one additional convolutional layer of the neural network different from the first convolutional layer to generate a medical image of the patient; and
displaying the medical image of the patient for clinical analysis.

9. The computer-readable medium of claim 8, wherein the first convolutional layer has a kernel of two and a stride of two.

10. The computer-readable medium of claim 8, wherein the input vector comprises a one-dimensional vector and the first convolutional layer comprises a one-dimensional convolutional layer.

11. The computer-readable medium of claim 8, wherein applying the filtered input vector to the at least one fully connected layer of the neural network to generate the matrix comprises:
applying the filtered input vector to a first hidden layer activated by a first activation function; and
applying an output of the first hidden layer to a second hidden layer activated by a second activation function to generate the matrix.

12. The computer-readable medium of claim 8, wherein applying the matrix to the at least one additional convolutional layer of the neural network different from the first convolutional layer to generate the medical image of the patient comprises:
applying the matrix to a second convolutional layer to filter the matrix in accordance with a first filter;
applying an output of the second convolutional layer to a third convolutional layer to filter the output of the second convolutional layer in accordance with a second filter; and
applying an output of the third convolutional layer to an output layer to generate the medical image of the patient.

13. The computer-readable medium of claim 8, wherein the raw sensor data comprises raw magnetic resonance imaging (MM) k-space data.

14. The computer-readable medium of claim 8, wherein the neural network comprises a data-driven, manifold learning neural network.

15. A system comprising:
a display;
one or more sensors;
one or more processors; and
one or more non-transitory computer readable storage media having instructions stored thereon that, when executed by the one or more processors, cause the one or more processors to implement operations comprising:
receiving raw sensor data acquired from a patient from the one or more sensors;
applying the raw sensor data to an input layer of a neural network to generate an input vector, wherein the input layer of the neural network orders the input vector such that real components and imaginary components of samples in the raw sensor data are adjacent;
applying the input vector to a first convolutional layer of the neural network to generate a filtered input vector;
applying the filtered input vector to at least one fully connected layer of the neural network to generate a matrix;
applying the matrix to at least one additional convolutional layer of the neural network different from the first convolutional layer to generate a medical image of the patient; and
causing the display to display the medial image of the patient for clinical analysis.

16. The system of claim 15, wherein:
the first convolutional layer has a kernel of two and a stride of two;
the input vector comprises a one-dimensional vector; and
the first convolutional layer comprises a one-dimensional convolutional layer.

17. The system of claim 15, wherein applying the filtered input vector to the at least one fully connected layer of the neural network to generate the matrix comprises:
applying the filtered input vector to a first hidden layer activated by a first activation function; and
applying an output of the first hidden layer to a second hidden layer activated by a second activation function to generate the matrix.

18. The system of claim 17, wherein applying the matrix to the at least one additional convolutional layer of the neural network different from the first convolutional layer to generate the medical image of the patient comprises:
applying the matrix to a second convolutional layer to filter the matrix in accordance with a first filter;
applying an output of the second convolutional layer to a third convolutional layer to filter the output of the second convolutional layer in accordance with a second filter; and
applying an output of the third convolutional layer to an output layer to generate the medical image of the patient.

19. The system of claim 15, wherein the raw sensor data comprises raw magnetic resonance imaging (MRI) k-space data.

20. The system of claim 15, wherein the neural network comprises a data-driven, manifold learning neural network.

* * * * *

UNITED STATES PATENT AND TRADEMARK OFFICE
CERTIFICATE OF CORRECTION

| | | |
|---|---|---|
| PATENT NO. | : 12,412,323 B2 | Page 1 of 1 |
| APPLICATION NO. | : 18/305697 | |
| DATED | : September 9, 2025 | |
| INVENTOR(S) | : Danyal Fareed Bhutto et al. | |

It is certified that error appears in the above-identified patent and that said Letters Patent is hereby corrected as shown below:

In the Claims

Claim 13, Line 3, Column 28, "imaging (MM) k-space data" should be --imaging (MRI) k-space data--.

Signed and Sealed this
Fourteenth Day of October, 2025

John A. Squires
*Director of the United States Patent and Trademark Office*